United States Patent
Stachel et al.

(10) Patent No.: US 10,287,293 B2
(45) Date of Patent: May 14, 2019

(54) BICYCLIC HETEROCYCLIC COMPOUNDS AS PDE2 INHIBITORS

(71) Applicants: Merck Sharp & Dohme Corp., Rahway, NJ (US); Shawn J. Stachel, Perkasie, PA (US); Christopher J. Sinz, South San Francisco, CA (US); Yili Chen, Hillsborough, NJ (US); Jonathan E. Wilson, West Orange, NJ (US); Michael P. Dwyer, Scotch Plains, NJ (US); Daniel V. Paone, Lansdale, PA (US); Shimin Xu, Beijing (CN)

(72) Inventors: Shawn J. Stachel, Perkasie, PA (US); Michael P. Dwyer, Scotch Plains, NJ (US); Christopher J. Sinz, South San Francisco, CA (US); Jonathan E. Wilson, West Orange, NJ (US); Daniel V. Paone, Lansdale, PA (US); Yili Chen, Hillsborough, NJ (US); Shimin Xu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/736,202

(22) PCT Filed: Jun. 27, 2016

(86) PCT No.: PCT/US2016/039479
§ 371 (c)(1),
(2) Date: Dec. 13, 2017

(87) PCT Pub. No.: WO2017/003895
PCT Pub. Date: Jan. 5, 2017

(65) Prior Publication Data
US 2018/0141952 A1    May 24, 2018

(30) Foreign Application Priority Data
Jul. 1, 2015 (WO) ............... PCT/CN2015/083059

(51) Int. Cl.
*C07D 487/04* (2006.01)
*A61P 25/28* (2006.01)
(Continued)

(52) U.S. Cl.
CPC ............ *C07D 487/04* (2013.01); *A61P 25/06* (2018.01); *A61P 25/16* (2018.01); *A61P 25/18* (2018.01); *A61P 25/22* (2018.01); *A61P 25/28* (2018.01)

(58) Field of Classification Search
CPC .......... A61P 25/06; A61P 25/16; A61P 25/18; A61P 25/22; A61P 25/28; C07D 487/04
See application file for complete search history.

(56) References Cited

U.S. PATENT DOCUMENTS

| 3,211,731 | A | | 10/1965 | Schmidt et al. |
| 3,840,537 | A | * | 10/1974 | Garside et al. .... C07D 253/075 544/184 |

(Continued)

FOREIGN PATENT DOCUMENTS

| CA | 2881806 | 2/2014 |
| EP | 1097706 A1 | 5/2001 |

(Continued)

OTHER PUBLICATIONS

Ahlstrom et al., Inactivation of Atrial Natriuretic Factor-Stimulated, Biochemical Pharmacology, 2000, 1133-1139, 59.
(Continued)

*Primary Examiner* — Erich A Leeser
(74) *Attorney, Agent, or Firm* — Sylvia A. Ayler; John C. Todaro

(57) ABSTRACT

The present invention is directed to dihydropyrazolopyrimidinone compounds of formulas (I) and (II) which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

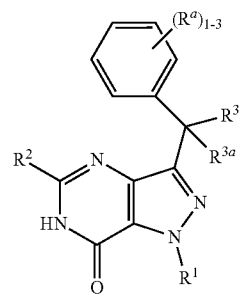

I

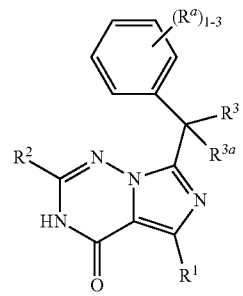

II

22 Claims, No Drawings

(51) Int. Cl.
  *A61P 25/22*   (2006.01)
  *A61P 25/18*   (2006.01)
  *A61P 25/16*   (2006.01)
  *A61P 25/06*   (2006.01)

(56) References Cited

U.S. PATENT DOCUMENTS

| | | |
|---|---|---|
| 6,534,511 B1 | 3/2003 | Campbell |
| 6,573,263 B2 | 6/2003 | Niewohner et al. |
| 8,598,155 B2 | 12/2013 | Helal et al. |
| 8,680,116 B2 | 3/2014 | DeLeon et al. |
| 2002/0132754 A1 | 9/2002 | Boss et al. |
| 2005/0009822 A1 | 1/2005 | Niewohner et al. |
| 2007/0135457 A1 | 6/2007 | Beyer et al. |
| 2009/0176829 A1 | 7/2009 | Verhoest et al. |
| 2012/0115885 A1 | 5/2012 | De Leon et al. |
| 2012/0214791 A1 | 8/2012 | Helal et al. |

FOREIGN PATENT DOCUMENTS

| | | |
|---|---|---|
| EP | 1097707 A1 | 5/2001 |
| WO | 2000021926 | 4/2000 |
| WO | WO2005061497 | 12/2003 |
| WO | WO2005041957 | 10/2004 |
| WO | WO2006024640 | 3/2006 |
| WO | WO200672615 | 7/2006 |
| WO | WO2009016498 | 2/2009 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012168817 | 12/2012 |
| WO | WO201300924 | 1/2013 |
| WO | WO2013034755 | 3/2013 |
| WO | WO2013098373 | 7/2013 |
| WO | WO2013110768 | 8/2013 |
| WO | 2013161913 | 10/2013 |
| WO | WO2014010732 | 1/2014 |
| WO | WO2014019979 | 2/2014 |
| WO | WO2014024125 | 2/2014 |
| WO | WO2014139983 | 9/2014 |
| WO | WO2015012328 | 1/2015 |
| WO | WO2015060368 | 4/2015 |
| WO | WO2005063723 | 7/2017 |

OTHER PUBLICATIONS

Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Wakabayashi et al., Involvement of Phosphodiesterase Isozymes in Osteoblastic, J. of Bone and Mineral Research, 2002, 249-253, 17.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate-Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Markwalder, Synthesis and Biological Evaluation of 1-Aryl-4,5-dihydro-1H-pyrazolo[3,4-d] pyrimidin-4-one Inhibitors of Cyclin-Dependent Kinases, J. Med. Chem, 2004, 5894-5911, 47.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.

(56) References Cited

OTHER PUBLICATIONS

Netherton et al., Vascular Endothelial Cell Cyclic Nucleotide phosphodiesterases and Regulated Cell Migration: IMplications in Angiogenesis, Molecular Pharmacology, 2005, 263-272, 67.

P. C. Tfelt-Hansen et al., One Hundred Years of Migraine Research: Major Clinical and, Headache, 2011, 752-778, 51.

Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.

Plummer et al., Discovery of potent selective bioavailable phosphodiesterase, Bioorganic & Medicinal Chemistry Letters, 2013, 3443-3447, 23.

Reierson et al., Repeated antidepressant therapy increases cyclic GMP signaling, Neurosci Letter, 2009, 149-153, 466 (3).

Rivet-Bastide et al., cGMP-stimulated Cyclic Nucleotide Phosphodiesterase Regulates the Basal, J. Clin. Invest, 1997, 2710-2718, 99.

Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.

Sanchez et al., Gas-Phase Tautomeric Equilibrium of 4-Hydroxypyrimidine, J. Am. Chem Soc., 2007, 6287-6290, 129.

Savai et al., Targeting Cancer with Phosphodiesterase Inhibitors, Expert Opinion, 2010, 117-131, 19.

Surapisitchat et al., Differential Regulation of Endothelial Cell Permeability by cGMP via Phosphodiesterases 2 and 3, Circulation Research, 2007, 811-818, 101.

Suvrana et al., Hydrolysis of N-Methyl-D-aspartate Receptor-Stimulated cAMP, J. of Pharmacology, 2002, 249-256, 302.

Van Staveren et al., The effects of phosphodiesterase inhibition on cyclic GMP and cyclic, Brain Research, 2001, 275-286, 888.

Vandecasteele, Cyclic GMP regulation of the L-type Ca2+ channel current, J. of Physiology, 2001, 329-340, 533.

Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.

* cited by examiner

BICYCLIC HETEROCYCLIC COMPOUNDS AS PDE2 INHIBITORS

CROSS REFERENCE TO RELATED APPLICATIONS

This application is the National Stage of International Application No. PCT/US2016/039479 filed on Jun. 27, 2016, which claims the benefit under International Application PCT/CN2015/083059 filed on Jul. 1, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001); platelet aggregation (R. J. Haslam, et Al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also US2007135457, WO00/21926, U.S. Pat. No. 3,211,731, WO2015060368, and J. Markwalder, et al., J. Med. Chem. 2004, 47, 5894-5911.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodiesterase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155, and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodiesterase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, Parkinson's disease, Parkinson's disease dementia (PDD) and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to bicyclic heterocyclic compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to bicyclic heterocyclic compounds of formulas I and II:

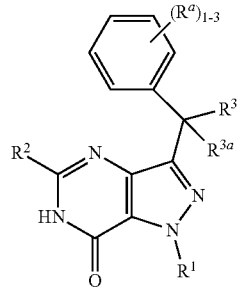

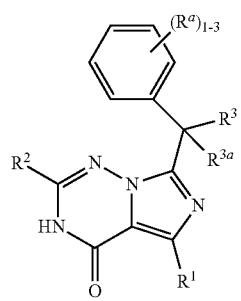

or a pharmaceutically acceptable salt thereof, wherein:

$R^1$ represents hydrogen, or $C_{1-6}$alkyl, said alkyl optionally substituted with 1 to 3 groups of $R^b$, $R^2$ represents OR, $NR_2$, $C_{1-6}$alkyl, $(CH_2)_{1-4}$OR, $C_{1-4}$haloalkyl, $C(O)C_{6-10}$aryl, $—(CH_2)_nC_{6-10}$aryl, $(CH_2)_nC_{3-10}$heterocyclyl or $(CH_2)_nC_{3-10}$cycloalkyl wherein when $R^2$ is a heterocyclyl it is attached to the pyrazolopyrimidinone or imidazotriazinone ring through a carbon atom, and wherein said alkyl, aryl, heterocyclyl and cycloalkyl are optionally substituted with 1 to 3 groups of $R^a$ $R^3$ and $R^{3a}$ independently represent hydrogen, $C_{1-6}$alkyl, or $C_{3-6}$cycloalkyl, said alkyl, and cycloalkyl, optionally substituted with 1 to 3 groups of $R^a$, or $R^3$ and $R^{3a}$ can combine with the carbon atom to which they are attached to form a $C_{3-6}$cycloalkyl, or $C_{4-10}$heterocycloalkyl, said alkyl, cycloalkyl, and heterocycloalkyl optionally substituted with 1 to 3 groups of $R^a$, R represents hydrogen, or $C_{1-6}$alkyl, $R^a$ is selected from the group consisting of hydrogen, halo, CN, $SCF_3$, $SF_5$, $C_{1-6}$alkyl, $(CH_2)_n$OR, $(CH_2)_nC_{1-4}$haloalkyl, O—$C_{1-4}$haloalkyl, $C_{3-6}$cycloalkyl, said alkyl and cycloalkyl optionally substituted with 1 to 3 groups of $C_{1-6}$alkyl or halo;

$R^b$ is selected from the group consisting of halo, CN, $C_{1-6}$alkyl, $(CH_2)_n$OR, $(CH_2)_nC_{1-4}$haloalkyl, O—$C_{1-4}$haloalkyl, and n represents 0, 1, 2, 3, or 4.

An embodiment of the invention of formula I and II is realized when $R^1$ is hydrogen.

An embodiment of the invention of formulas I and II is realized when $R^1$ is $C_{1-6}$alkyl, said alkyl optionally substituted with 1 to 3 groups of $R^b$. A subembodiment of this aspect of the invention is realized when optionally substituted $C_{1-6}$alkyl of $R^1$ is selected from the group consisting of $CH_3$, $CH_2OH$, $CH_2CH_2OH$, $CH_2CN$, $CH_2CF_3$, $CH_2CH_2F$, $CH_2CH_2CF_3$, $CH_2CHF_2$, $CH(CH_2OH)CH_3$. Another subembodiment of this aspect of the invention is realized when optionally substituted $C_{1-6}$alkyl $R^1$ is $CH_2OH$, $CH_2CH_2OH$, or $CH(CH_2OH)CH_3$. Still another embodiment of this aspect of the invention is realized when optionally substituted $C_{1-6}$alkyl of $R^1$ is $CH_2CF_3$, $CH_2CH_2F$, or $CH_2CH_2CF_3$. Yet another embodiment of this aspect of the invention is realized when C$_{1-6}$alkyl of R$^1$ is CH$_3$.

Another aspect of the invention of formulas I and II is realized when R$^2$ is optionally substituted C$_{1-6}$alkyl. A subembodiment of this aspect of the invention is realized when R$^2$ is selected from the group consisting (CH$_2$)$_n$CH$_3$, CH(CH$_3$)$_2$, and C(CH$_3$)$_3$. Still another subembodiment of this aspect of the invention is realized when R$^2$ is CH$_3$.

Another aspect of the invention of formulas I and II is realized when R$^2$ is OR. A subembodiment of this aspect of the invention is realized when R$^2$ is selected from the group OH, and optionally substituted C$_{1-6}$alkyl.

Another aspect of the invention of formulas I and II is realized when R$^3$ and R$^{3a}$ independently represent hydrogen or optionally substituted C$_{1-6}$alkyl. A subembodiment of this aspect of the invention is realized when R$^3$ and R$^{3a}$ independently represent hydrogen, CH$_3$, CH$_2$OH, CH$_2$CH$_2$OH, CH$_2$CN, CH$_2$CF$_3$, CH$_2$CH$_2$F, CH$_2$CH$_2$CF$_3$, CH$_2$CHF$_2$, CH(CH$_2$OH)CH$_3$. Another subembodiment of this aspect of the invention is realized when R$^3$ and R$^{3a}$ are CH$_3$. A subembodiment of this aspect of the invention is realized when one of R$^3$ and R$^{3a}$ is hydrogen and the other is selected from the group consisting of CH$_3$, CH$_2$OH, CH$_2$CH$_2$OH, CH$_2$CN, CH$_2$CF$_3$, CH$_2$CH$_2$F, CH$_2$CH$_2$CF$_3$, CH$_2$CHF$_2$, CH(CH$_2$OH)CH$_3$. Another subembodiment of this aspect of the invention is realized when one of R$^3$ and R$^{3a}$ is hydrogen and the other is CH$_3$.

Still another aspect of the invention of formulas I and II is realized when R$^3$ and R$^{3a}$ combine with the carbon atom to which they are attached to form a C$_{3-6}$cycloalkyl, or C$_{4-10}$heterocycloalkyl, said alkyl, cycloalkyl, and heterocycloalkyl optionally substituted with 1 to 3 groups of R$^a$. An embodiment of this aspect of the invention is realized when R$^3$ and R$^{3a}$ combine to form an optionally substituted cyclopropyl, cyclobutyl, cyclopentyl or cyclohexyl.

Another embodiment of the invention of formulas I and II is realized when R$^a$ is selected from OH, halo, (CH$_2$)$_n$CH$_3$, CH(CH$_3$)$_2$, C(CH$_3$)$_3$, (CH$_2$)$_n$OCH$_3$, OCH(CH$_3$)$_2$, CH$_2$F, CHF$_2$, (CH$_2$)$_n$CF$_3$, CF$_2$CH$_3$, OCHF$_2$, OCF$_3$, CF$_2$CF$_3$, cyclobutyl, cyclopropyl said groups optionally substituted with 1 to 3 groups of C$_{1-6}$alkyl or halo.

Still another embodiment of the invention of formula I and II is realized when at least one of R$^a$ is CF$_3$.

Another embodiment of the invention of formula I and II is realized when n is 0. Another embodiment of the invention of formula I is realized when n is 1. Another embodiment of the invention of formula I and II is realized when n is 2. Another embodiment of the invention of formula I and II is realized when n is 3. Still another embodiment of the invention of formula I and II is realized when n of R$^a$ is 0-1, 0-2, or 0-3.

Still another embodiment of the invention of formula I is realized when it is represented by structural formula Ia:

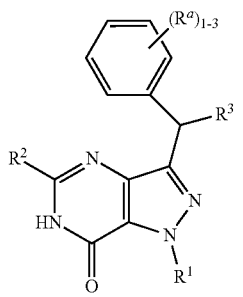

Ia or a pharmaceutically acceptable salt thereof wherein R$^1$, R$^2$, R$^3$, and R$^a$ are as previously described.

An aspect of the invention of formula Ia is realized when R$^1$ is optionally substituted C$_{1-6}$alkyl selected from the group consisting of CH$_3$, CH$_2$CH$_2$OH, CH$_2$CN, CH$_2$CF$_3$, CH$_2$CH$_2$F, CH$_2$CH$_2$CF$_3$, CH(CH$_2$OH)CH$_3$, and R$^a$ is selected from OH, halo, (CH$_2$)$_n$CH$_3$, CH(CH$_3$)$_2$, C(CH$_3$)$_3$, (CH$_2$)$_n$OCH$_3$, OCH(CH$_3$)$_2$, CH$_2$F, CHF$_2$, (CH$_2$)$_n$CF$_3$, CF$_2$CH$_3$, OCHF$_2$, OCF$_3$, CF$_2$CF$_3$, cyclobutyl, cyclopropyl said groups optionally substituted with 1 to 3 groups of C$_{1-6}$alkyl or halo.

Another aspect of the invention of formula Ia is realized when R$^2$ is optionally substituted C$_{1-6}$alkyl. A subembodiment of this aspect of the invention is realized when R$^2$ is selected from the group consisting (CH$_2$)$_n$CH$_3$, CH(CH$_3$)$_2$, and C(CH$_3$)$_3$. Still another subembodiment of this aspect of the invention is realized when R$^2$ is CH$_3$.

Another aspect of the invention of formula Ia is realized when R$^2$ is selected from the group consisting OR, and NR$_2$. A subembodiment of this aspect of the invention is realized when R$^2$ is selected from OH, O—C$_{1-6}$alkyl, NH$_2$, NH(CH$_3$), and N(CH$_3$)$_2$.

Another aspect of the invention of formulas Ia is realized when R$^3$ is optionally substituted C$_{1-6}$alkyl. A subembodiment of this aspect of the invention is realized when the optionally substituted alkyl of R$^3$ is methyl, ethyl, propyl, isopropyl, butyl, CH$_2$OH, CH$_2$CH$_2$OH, CH$_2$CN, CH$_2$CF$_3$, CH$_2$CH$_2$F, CH$_2$CH$_2$CF$_3$, CH$_2$CHF$_2$, or CH(CH$_2$OH)CH$_3$. Another subembodiment of this aspect of the invention is realized when R$^3$ is methyl.

Still another aspect of the invention of formula Ia is realized when R$^1$ is optionally substituted C$_{1-6}$alkyl selected from the group consisting of CH$_3$, CH$_2$CH$_2$OH, CH$_2$CN, CH$_2$CF$_3$, CH$_2$CH$_2$F, CH$_2$CH$_2$CF$_3$, CH(CH$_2$OH)CH$_3$, R$^2$ is selected from the group consisting OR, NR$_2$, (CH$_2$)$_n$CH$_3$, CH(CH$_3$)$_2$, and C(CH$_3$)$_3$, R$^3$ is selected from the group consisting of CH$_3$, CH$_2$OH, CH$_2$CH$_2$OH, CH$_2$CN, CH$_2$CF$_3$, CH$_2$CH$_2$F, CH$_2$CH$_2$CF$_3$, CH$_2$CHF$_2$, and CH(CH$_2$OH)CH$_3$ and R$^a$ is selected from OH, halo, (CH$_2$)$_n$CH$_3$, CH(CH$_3$)$_2$, C(CH$_3$)$_3$, (CH$_2$)$_n$OCH$_3$, OCH(CH$_3$)$_2$, CH$_2$F, CHF$_2$, (CH$_2$)$_n$CF$_3$, CF$_2$CH$_3$, OCHF$_2$, OCF$_3$, CF$_2$CF$_3$, cyclobutyl, cyclopropyl said groups optionally substituted with 1 to 3 groups of C$_{1-6}$alkyl or halo. A subembodiment of this aspect of the invention is realized when R$^2$ and R$^3$ are CH$_3$.

Another aspect of the invention of formula Ia is realized when at least one R$^a$ is CF$_3$ and is present at the para position relative to the alkyl linker. Another aspect of the invention of formula Ia is realized when at least one R$^a$ is C(CH$_3$)$_3$ and is present at the para position relative to the alkyl linker.

Still another embodiment of the invention of the compounds of formula II is represented by structural formula IIa:

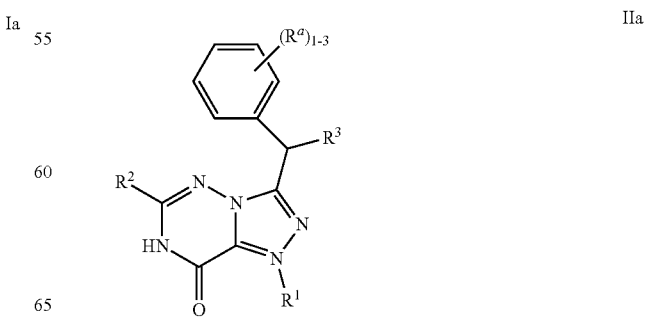

IIa or a pharmaceutically acceptable salt thereof wherein $R^1$, $R^2$, $R^3$, and $R^a$ are as previously described.

An aspect of the invention of formula IIa is realized when $R^1$ is optionally substituted $C_{1-6}$alkyl selected from the group consisting of $CH_3$, $CH_2OH$, $CH_2CH_2OH$, $CH_2CN$, $CH_2CF_3$, $CH_2CH_2F$, $CH_2CH_2CF_3$, $CH(CH_2OH)CH_3$, and $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_n$ $CF_3$, $CF_2CH_3$, $OCHF_2$, $OCF_3$, $CF_2CF_3$, cyclobutyl, cyclopropyl said groups optionally substituted with 1 to 3 groups of $C_{1-6}$alkyl or halo.

Another aspect of the invention of formula IIa is realized when $R^2$ is optionally substituted $C_{1-6}$alkyl. A subembodiment of this aspect of the invention is realized when $R^2$ is selected from the group consisting $(CH_2)_nCH_3$, $CH(CH_3)_2$, and $C(CH_3)_3$. Still another subembodiment of this aspect of the invention is realized when $R^2$ is $CH_3$.

Another aspect of the invention of formula IIa is realized when $R^2$ is selected from the group consisting OR, and $NR_2$. A subembodiment of this aspect of the invention is realized when $R^2$ is selected from OH, O—$C_{1-6}$alkyl, $NH_2$, $NH(CH_3)$, and $N(CH_3)_2$.

Another aspect of the invention of formula IIa is realized when $R^3$ is optionally substituted $C_{1-6}$alkyl. A subembodiment of this aspect of the invention is realized when the optionally substituted alkyl of $R^3$ is methyl, ethyl, propyl, isopropyl, butyl, $CH_2OH$, $CH_2CH_2OH$, $CH_2CN$, $CH_2CF_3$, $CH_2CH_2F$, $CH_2CH_2CF_3$, $CH_2CHF_2$, or $CH(CH_2OH)CH_3$. Another subembodiment of this aspect of the invention is realized when $R^3$ is methyl.

Still another aspect of the invention of formula IIa is realized when $R^1$ is optionally substituted $C_{1-6}$alkyl selected from the group consisting of $CH_3$, $CH_2OH$, $CH_2CH_2OH$, $CH_2CN$, $CH_2CF_3$, $CH_2CH_2F$, $CH_2CH_2CF_3$, $CH(CH_2OH)CH_3$, $R^2$ is selected from the group consisting OR, $NR_2$, $(CH_2)_nCH_3$, $CH(CH_3)_2$, and $C(CH_3)_3$, $R^3$ is selected from the group consisting of $CH_3$, $CH_2OH$, $CH_2CH_2OH$, $CH_2CN$, $CH_2CF_3$, $CH_2CH_2F$, $CH_2CH_2CF_3$, $CH_2CHF_2$, and $CH(CH_2OH)CH_3$ and $R^a$ is selected from OH, halo, $(CH_2)_n$ $CH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$alkyl or halo. A subembodiment of this aspect of the invention is realized when $R^2$ and $R^3$ are $CH_3$.

Another aspect of the invention of formula IIa is realized when at least one $R^a$ is $CF_3$ and is present at the para position relative to the alkyl linker. Another aspect of the invention of formula IIa is realized when at least one $R^a$ is $C(CH_3)_3$ and is present at the para position relative to the alkyl linker.

The invention is also directed to a method for the treatment of central nervous system disorders associated with phosphodiesterase 2 (PDE2) using the compounds of Formula I and II. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formulas I and II.

Examples of compounds of the invention can be found throughout the specification.

The invention also encompasses pharmaceutical compositions containing a compound of formula I, and methods for treatment or prevention of phosphodiesterase mediated diseases using compounds of formulas I and II.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency is permissible.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

It should be appreciated by anyone skilled in the art that the compounds of this invention can exist in several tautomeric forms as shown below:

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I, Ia and II, IIa and they are intended to represent all possible tautomeric forms for these compounds without regard to what actually is the predominant tautomeric form in existence for a particular compound.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae I, Ia, II and IIa and pharmaceutically acceptable salts thereof.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention

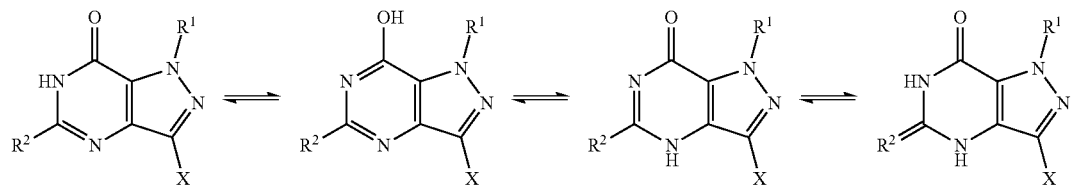

Tautomer IA

Tautomer IA is possible when $R^2$ = O or NR

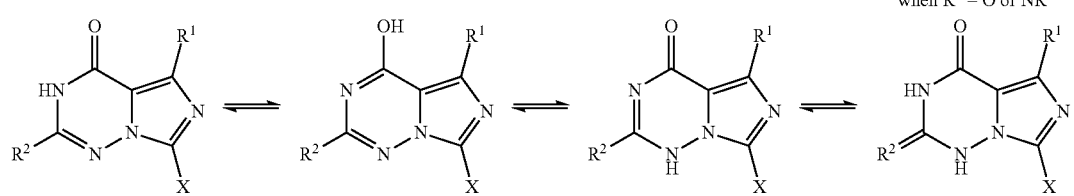

Tautomer IIA

Tautomer IIA is possible when $R^2$ = O or NR is meant to encompass that particular isomer in pure form or as part of a mixture with other isomers in any proportion.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulas I, II, Ia, and IIa. For example, isotopic forms of hydrogen (H), including protium ($^1H$) and deuterium ($^2H$); isotopic forms of carbon, including $^{11}C$; and isotopic forms of fluorine, including $^{18}F$. Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. While $^{12}C$ and $^{19}F$ are the predominant isotopes of carbon and fluorine found in nature, enriching for $^{11}C$ or $^{18}F$ may afford advantages, particularly for use in imaging via positron emission tomography (PET). In general, one of ordinary skill in the art would appreciate that a preferred substance for potential use as a PET imaging agent would effectively inhibit the PDE2 enzyme with a Ki value less than or about 0.5 nM, where compounds tested are comprised of naturally occurring isotopes. Such preferred substances, when enriched with $^{11}C$ or $^{18}F$, may be therefore useful as PET imaging agents. Isotopically enriched compounds within generic formulas I, II, Ia, and IIa can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DCM=dichloromethane
DEA=diethylamine
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate Ph=phenyl
PPTS=pyridinium p-toluene sulfonate
pTSA=p-toluene sulfonic acid
PyH.Br3=pyridine hydrobromide perbromide
r.t./RT=room temperature
rac.=racemic
T3P=2,4,6-tripropyl-1,3,5,2,4,6-trioxatriphosphinane 2,4,6-trioxide
TBAF=tetrabutylammonium fluoride
TFA=trifluoroacetic acid
TfO=trifluoromethanesulfonate=triflate
THF=tetrahydrofuran
TLC=thin layer chromatography
TMSCl=trimethylsilyl chloride All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEi's such as (Aricept (donepezil)) and Exelon (rivastigmine) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suprocline, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, t-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwisely noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 µM $NH_4HCO_3$), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

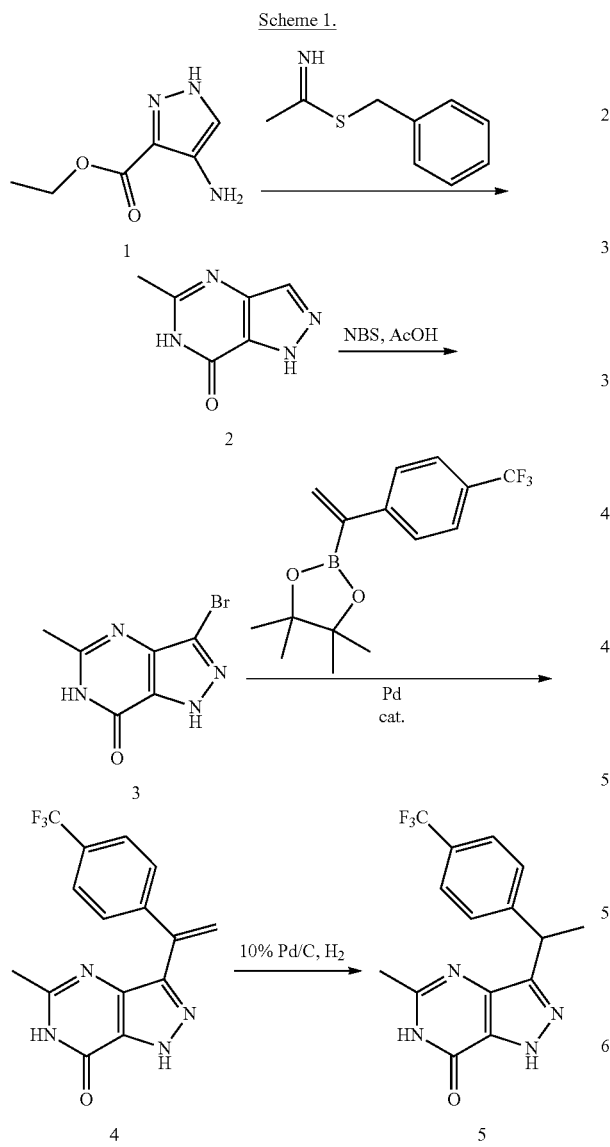

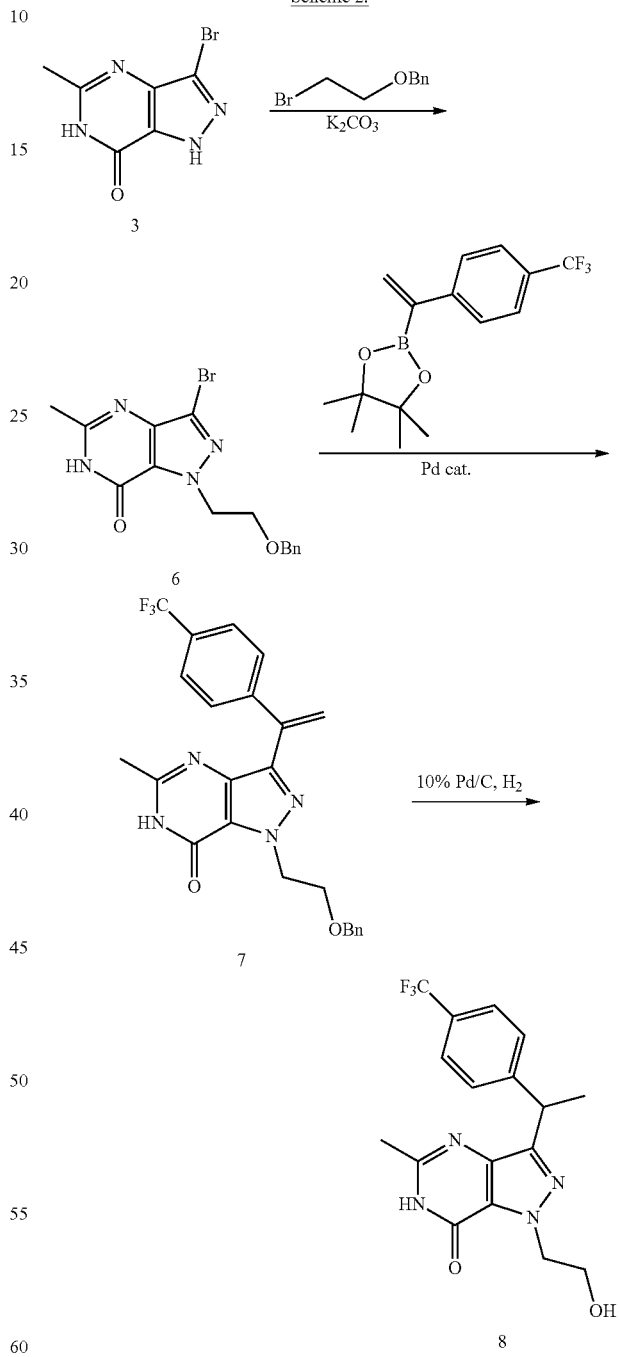

Scheme 1 illustrates a synthetic sequence for the preparation of pyrazolopyrimidinones such as 5 from pyrazole amino ester 1. Cyclization of 1 with benzyl ethanimidothioate hydrochloride should afford 2 which can be subjected to NBS to furnish bromide 3. Treatment of 3 with a vinyl boronate in the presence of a palladium catalyst should afford 4 which can be treated under hydrogenation conditions to furnish pyrazolopyrimidinone 5.

Scheme 2 illustrates a synthetic sequence for the preparation of pyrazolopyrimidinones such as 8 from bromide 3. Treatment of 3 with base in the presence of a primary bromide should furnish 6 which can be subjected to palladium-catalyzed Suzuki coupling with a vinyl boronate to furnish 7. Treatment of 7 with 10% palladium on carbon in the presence of hydrogen will furnish pyrazolopyrimidinone 8.

Scheme 3.

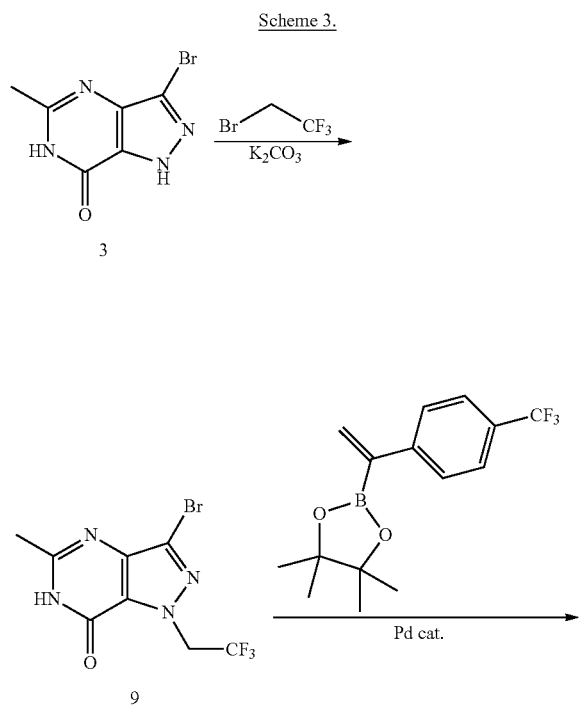

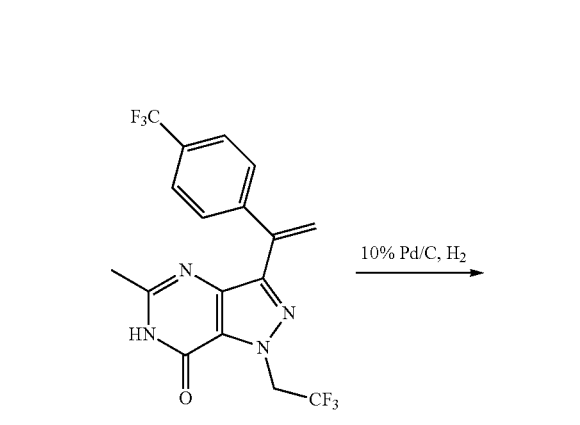

Scheme 3 illustrates a synthetic sequence for the preparation of trifluoromethyl-bearing pyrazolopyrimidinones such as 11 from bromide 3. Treatment of 3 with base in the presence of a 2-bromo-1,1,1-trifluoroethane should furnish 9 which can be subjected to palladium-catalyzed Suzuki coupling with a vinyl boronate to furnish 10. Treatment of 10 with 10% palladium on carbon in the presence of hydrogen will furnish trifluoroethyl pyrazolopyrimidinone 11.

Scheme 4.

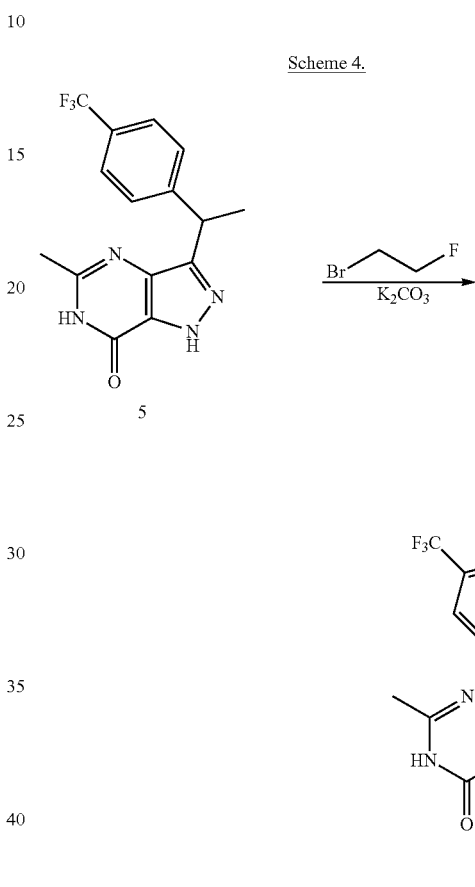

Scheme 4 illustrates a synthetic sequence for the preparation of fluoroethyl-bearing pyrazolopyrimidinones such as 12 which can be prepared from 5 by treatment with 1-bromo-2-fluoroethane in the presence of base.

Scheme 5.

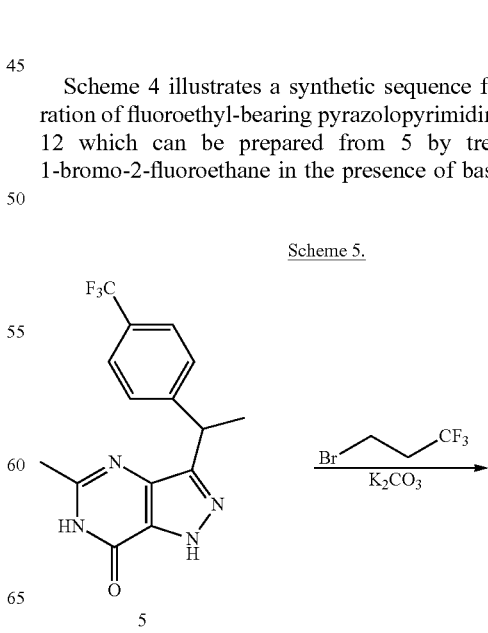

29

-continued

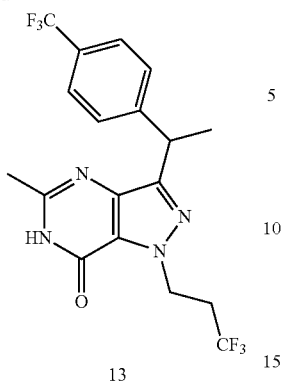

13

Scheme 5 illustrates a synthetic sequence for the preparation of trifluoroethyl-bearing pyrazolopyrimidinones such as 13 which can be prepared from 5 by treatment with 3-bromo-1,1,1-trifluoropropane in the presence of base.

30

-continued

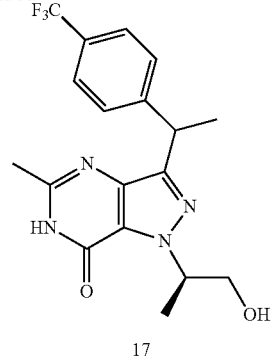

17

Scheme 6 illustrates a synthetic sequence for the preparation of substituted ethanol bearing pyrazolopyrimidinones such as 17 from bromide 3. Treatment of 3 with base in the presence of an enantiomerically enriched secondary bromide 14 should furnish 15 which can be subjected to palladium-catalyzed Suzuki coupling with a vinyl boronate to furnish 16. Treatment of 16 with 10% palladium on carbon in the presence of hydrogen will furnish substituted ethanol-bearing pyrazolopyrimidinone 17.

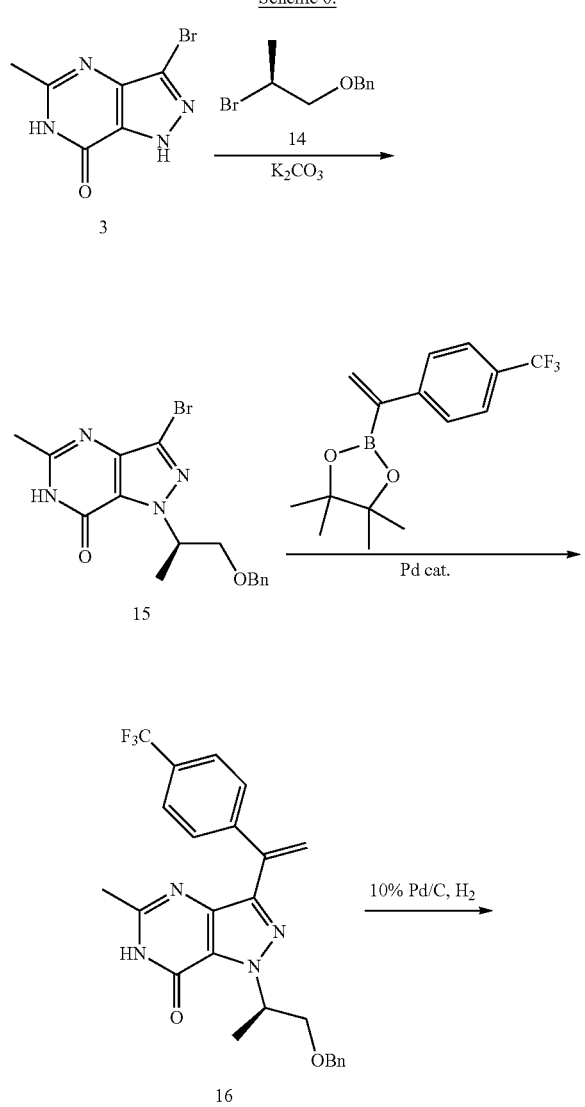

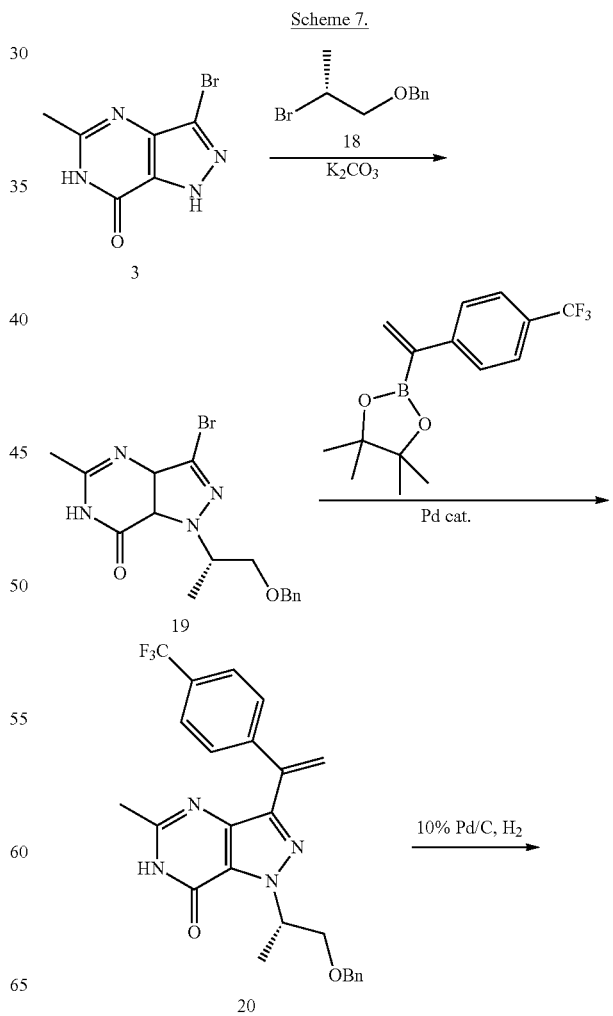

-continued

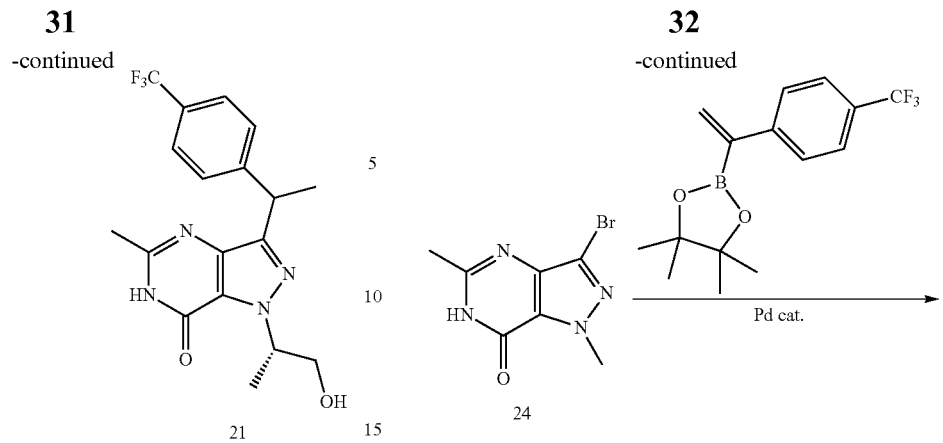

Scheme 7 illustrates a synthetic sequence for the preparation of substituted ethanol bearing pyrazolopyrimidinones such as 21 from bromide 3. Treatment of 3 with base in the presence of an enantiomerically enriched secondary bromide 18 should furnish 19 which can be subjected to palladium-catalyzed Suzuki coupling with a vinyl boronate to furnish 20. Treatment of 20 with 10% palladium on carbon in the presence of hydrogen will furnish substituted ethanol-bearing pyrazolopyrimidinone 21.

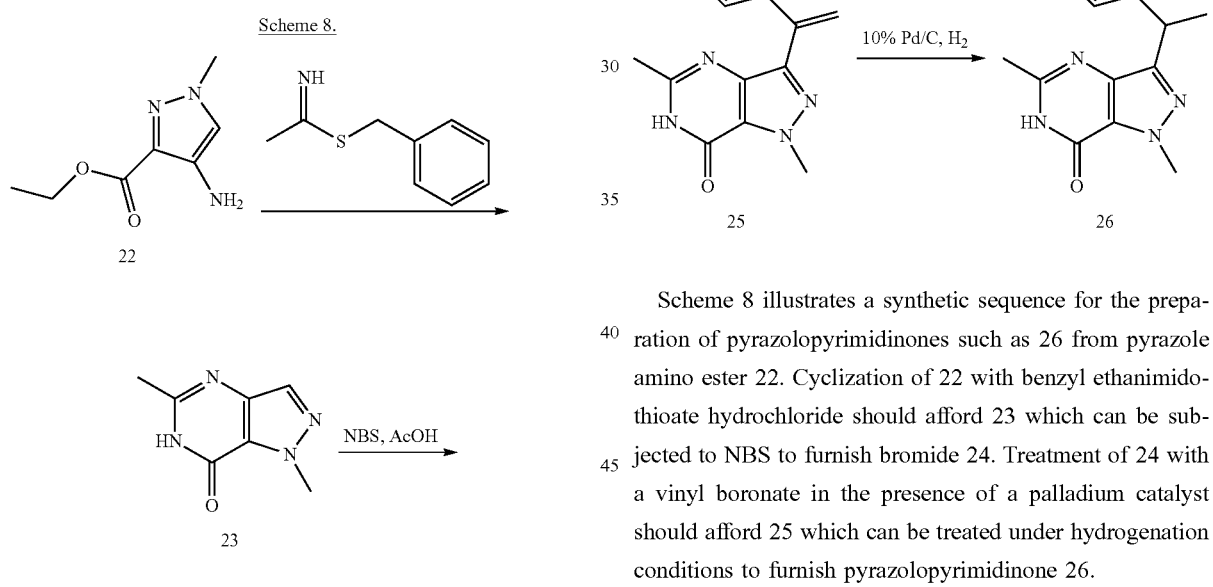

Scheme 8 illustrates a synthetic sequence for the preparation of pyrazolopyrimidinones such as 26 from pyrazole amino ester 22. Cyclization of 22 with benzyl ethanimidothioate hydrochloride should afford 23 which can be subjected to NBS to furnish bromide 24. Treatment of 24 with a vinyl boronate in the presence of a palladium catalyst should afford 25 which can be treated under hydrogenation conditions to furnish pyrazolopyrimidinone 26.

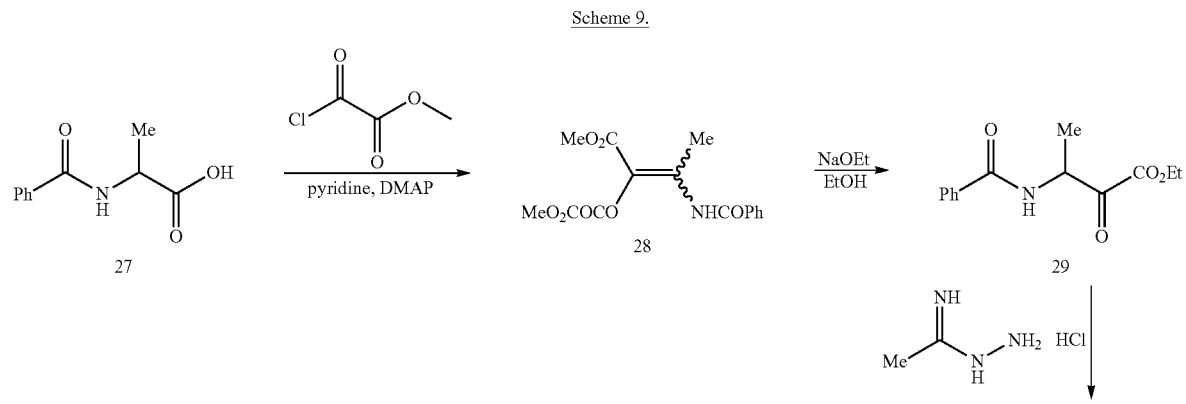

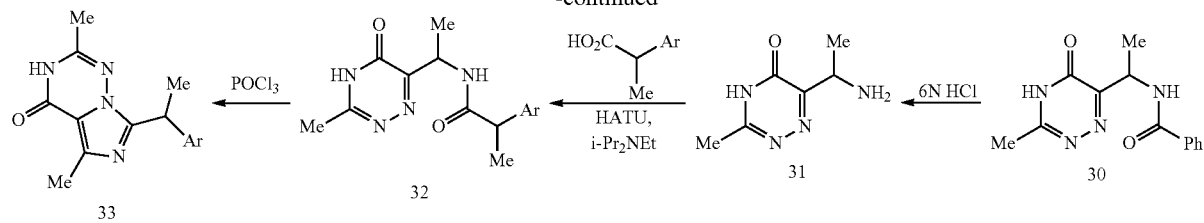

Scheme 9 illustrates a synthetic sequence for the preparation of imidazo[5,1-f][1,2,4]triazin-4(3H)-ones such as 33. The amino-triazinone intermediate 31 can be prepared in 4 steps from N-benzoyl amino acids such as 27. Coupling of intermediate 31 to arylacetic acid derivatives provides amido triazinone intermediates such as 32 with can be converted to imidazotriazinone derivatives such as 33 via dehydration with phosphorous oxychloride.

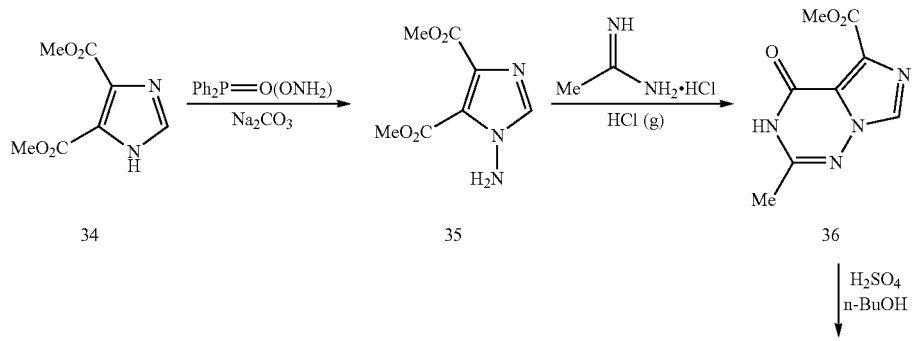

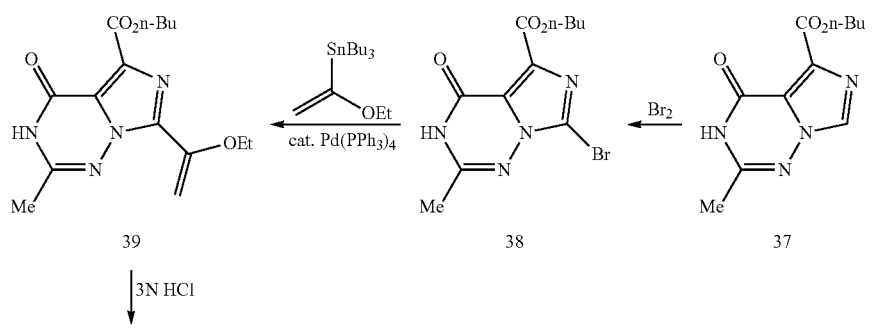

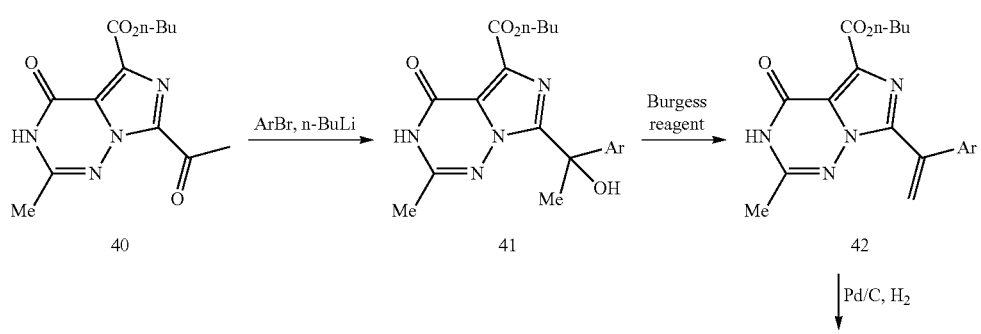

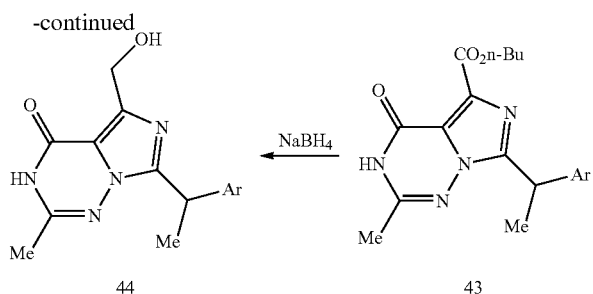

Scheme 10 illustrates a synthetic sequence for the preparation of imidazo[5,1-f][1,2,4]triazin-4(3H)-ones such as 44. The intermediate ketone 40 can be prepared from dimethyl imidazoledicarboxylate 34 in 6 steps. Addition of an organometallic reagent to ketone 40 provides the tertiary alcohol intermediate 41. Dehydration of 41 provides olefin intermediate 42 which can be reduced with hydrogen via palladium catalysis to afford the penultimate ester intermediate 43. Reduction of 43 with lithium borohydride provides imidazotriazinone alcohol derivatives such as 44.

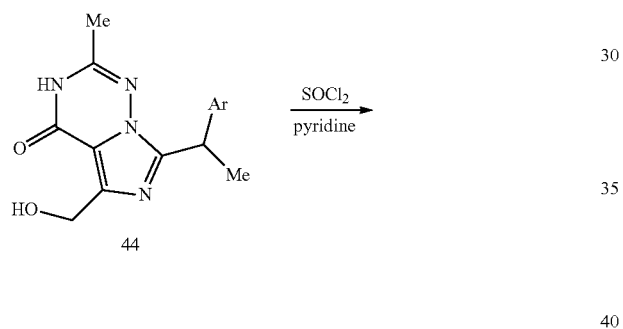

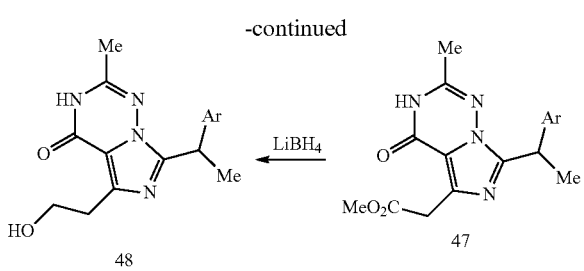

Scheme 11 illustrates a synthetic sequence for the homologation of imidazotriazinone alcohol derivatives such as 44 in 4 steps to provide homologated imidazotriazinone derivatives such as 48.

PREPARATIVE EXAMPLES

Preparatory Example 1

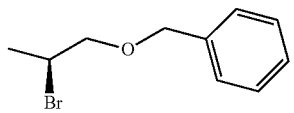

(S)-((2-Bromopropoxy)methyl)benzene

To a solution of imidazole (0.98 g, 14.4 mmol) and triphenylphosphine (3.8 g, 14.4 mmol) in DCM (67 mL) under $N_2$ at 0° C. was added bromine (0.74 ml, 14.4 mmol) dropwise. (R)-1-(Benzyloxy)propan-2-ol (2.0 g, 12.0 mmol) was then added slowly to the mixture which was allowed to warm to RT and stir for 12 h. The mixture was concentrated and was diluted with hexane/EtOAc (4:1, 430 mL). The solution was filtered through a short pad silica gel and the filtrated was concentrated under reduced pressure to afford the title compound as a solid which was used without purification. $^1$H NMR (CDCl$_3$, 500 MHz) δ: 7.72 (m, 2H), 7.59 (m, 1H), 7.45 (m, 2H), 4.62 (s, 2H), 4.21 (m, 1H), 3.71 (m, 1H), 3.62 (m, 1H), 2.81 (m, 2H), 1.76 (d, J=6.5 Hz, 3H).

Preparatory Example 2

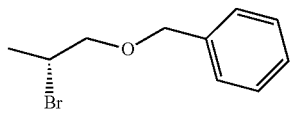

(R)-((2-Bromopropoxy)methyl)benzene

The title compound was prepared using (S)-1-(benzyloxy) propan-2-ol and the procedure set forth in Preparatory Example 1 as a solid which was used without purification. $^1$H NMR (CDCl$_3$, 500 MHz) δ: 7.72 (m, 2H), 7.59 (m, 1H), 7.45 (m, 2H), 4.61 (s, 2H), 4.20 (m, 1H), 3.71 (m, 1H), 3.62 (m, 1H), 2.81 (m, 2H), 1.76 (d, J=6.5 Hz, 3H).

Examples 1 and 2

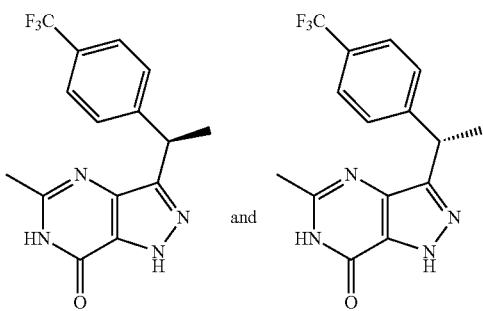 [SMILES: Cc1nc2c([C@H](C)c3ccc(C(F)(F)F)cc3)n[nH]c2c(=O)[nH]1 ; Cc1nc2c([C@@H](C)c3ccc(C(F)(F)F)cc3)n[nH]c2c(=O)[nH]1]

(R)- or (S)-5-Methyl-3-(1-(4-(trifluoromethyl)phenyl)ethyl)-1H-pyrazolo[4,3-d]pyrimidin-7(6H)-one (Scheme 1)

Step 1—5-Methyl-1H-pyrazolo[4,3-d]pyrimidin-7(6H)-one

To a solution of ethyl 4-amino-1H-pyrazole-5-carboxylate (2.3 g, 14.8 mmol) in pyridine (25 mL) under N$_2$ at rt was added benzyl ethanimidothioate hydrochloride (3.0 g, 14.8 mmol). The mixture was affixed with a reflux condenser, heated to 115° C., and stirred overnight at this temperature. The mixture was cooled to rt and was concentrated under reduced pressure to afford a residue that was suspended in EtOH (30 mL) and H$_2$O (10 mL). The mixture was treated with 1 M NaOH until pH~7 and the resultant solid was filtered off. The solid was washed with water and dried under high vacuum overnight to afford the title compound as a solid. $^1$H NMR (DMSO, 500 MHz) δ: 8.92 (s, 1H), 8.01 (br s, 2H), 2.45 (s, 3H). MS=151.1 (M+H)$^+$.

Step 2. 3-Bromo-5-methyl-H-pyrazolo[4,3-d]pyrimidin-7(6H)-one

To a suspension of 5-methyl-1H-pyrazolo[4,3-d]pyrimidin-7(6H)-one (1.5 g, 10 mmol) in CH$_3$CN (30 mL) under N$_2$ at rt was added glacial acetic acid (0.14 ml, 2.5 mmol) followed by addition of NBS (2.13 g, 12.0 mmol). The suspension mixture was heated to 80° C. and was stirred for 2 h. The mixture was cooled to room temperature and the resultant precipitate was collected by filtration. This material was dried under high vacuum overnight to afford the title compound as a solid. MS=231.2 (M+H)$^+$.

Step 3. 5-Methyl-3-(1-(4-(trifluoromethyl)phenyl)vinyl)-1H-pyrazolo[4,3-d]pyrimidin-7(6H)-one To a suspension of 3-bromo-5-methyl-1H-pyrazolo[4,3-d]pyrimidin-7(6H)-one (500 mg, 2.18 mmol) and 4,4,5,5-tetramethyl-2-(1-(4-(trifluoromethyl)phenyl)vinyl)-1,3,2-dioxaborolane (976 mg, 3.27 mmol), palladium (II) acetate (245 mg, 1.092 mmol), sodium 3,3',3''-phosphinetriyltribenzenesulfonate hydrate (1.92 g, 3.27 mmol) in DMF (1.5 mL) and water (0.5 mE) at rt under N$_2$ was added diisopropylamine (0.78 ml, 5.5 mmol) dropwise. The mixture was heated to 80° C., stirred for 2 h, and was recooled to RT. The mixture was filtered through a pad of Celite™ and the resulting filtrate was concentrated under reduced pressure. The residue was purified by reverse-phase HPLC chromatography (SureFire C18, 30-90% ACN in water (0.5% TFA)) to afford the title compound as a solid. MS=321.1 (M+H)$^+$.

Step 4 (R)- or (S)-5-Methyl-3-(1-(4-(trifluoromethyl)phenyl)ethyl)-1H-pyrazolo[4,3-d]pyrimidin-7(6H)-one To a solution of 5-methyl-3-(1-(4-(trifluoromethyl)phenyl)vinyl)-1H-pyrazolo[4,3-d]pyrimidin-7(6H)-one (40 mg, 0.13 mmol) in EtOH (1 mL) was added 10% Pd—C(40 mg, 0.037 mmol) in one portion. The result mixture was evacuated, filled with H$_2$, and was stirred under a H$_2$ balloon for 2 h. The mixture was purged to N$_2$, filtered thru a pad of Celite™, and the pad was washed with EtOH. The resulting filtrate was concentrated under reduced pressure and the resultant residue was purified by reverse-phase HPLC chromatography (SureFire C18 column, 30-90% ACN in water (0.05% TFA)) to yield the racemic title compound as a solid. The enantiopure title compounds were obtained by chiral SFC chromatography (AD column, 25% IPA (0.2% DEA)/CO$_2$). The faster eluting enantiomer of the title compound (Example 1) was obtained as a solid. $^1$H NMR (CDCl$_3$, 500 MHz) δ: 7.59 (m, 4H), 4.71 (m, 1H), 2.53 (s, 3H), 1.82 (d, J=7.3 Hz, 3H). MS=323.2 (M+H)$^+$. The slower-eluting enantiomer of the title compound (Example 2) was obtained as a solid. $^1$H NMR (CDCl$_3$, 500 MHz) δ: 7.59 (m, 4H), 4.71 (m, 1H), 2.53 (s, 3H), 1.82 (d, J=7.3 Hz, 3H). MS=323.2 (M+H)$^+$.

Examples 3 and 4

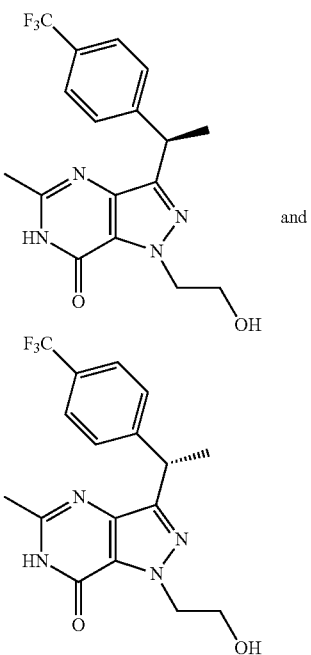

(R)- or (S)-1-(2-Hydroxyethyl)-5-methyl-3-(1-(4-(trifluoromethyl)phenyl)ethyl)-1H-pyrazolo[4,3-d]pyrimidin-7(6H)-one (Scheme 2)

Step 1. 1-(2-(Benzyloxy)ethyl)-3-bromo-5-methyl-1H-pyrazolo[4,3-d]pyrimidin-7(6H)-one To a suspension of 3-bromo-5-methyl-1H-pyrazolo[4,3-d]pyrimidin-7(6H)-one (100 mg, 0.44 mmol) from step 2 of Examples 1 and 2 in DMF (1 mL) under $N_2$ at rt was added $K_2CO_3$ (91 mg, 0.66 mmol) followed by addition of ((2-bromoethoxy)methyl)benzene (94 mg, 0.44 mmol). The mixture heated to 75° C., stirred for 30 min, and was recooled to rt. The mixture was concentrated under reduced pressure and the resultant residue was purified by reverse-phase HPLC chromatography (SureFire C18 column, 10-90% ACN in water (0.05% TFA)) to afford the title compound as a solid. MS=365.0 $(M+H)^+$.

Step 2. 1-(2-(Benzyloxy)ethyl)-5-methyl-3-(1-(4-(trifluoromethyl)phenyl)vinyl)-1H-pyrazolo[4,3-d]pyrimidin-7(6H)-one To a solution of 1-(2-(benzyloxy)ethyl)-3-bromo-5-methyl-1H-pyrazolo[4,3-d]pyrimidin-7(6H)-one (90 mg, 0.25 mmol) in NMP (2.4 mL) at RT was added 4,4,5,5-tetramethyl-2-(1-(4-(trifluoromethyl)phenyl)vinyl)-1,3,2-dioxaborolane (0.15 g, 0.50 mmol), [4-(di-tert-butylphosphino)-N,N-dimethylaniline-2-(2'-aminobiphenyl)] palladium (II) methanesulfonate (1.6 mg, 2.5 µmol) [APhos Pd G3, Aldrich] and a 1 M solution of $K_3PO_4$ (0.74 ml, 0.74 mmol). The resulting heterogenous mixture was heated to 80° C. and was stirred at this temperature overnight. The mixture was cooled to RT, filtered, and the filtrate was concentrated under reduced pressure. The residue was purified by reverse-phase chromatography (SureFire C18 column, 30-90% ACN in water (0.05% TFA)) to afford the title compound as a solid. MS=455.1 $(M+H)^+$.

Step 3. (R)- or (S)-1-(2-Hydroxyethyl)-5-methyl-3-(1-(4-(trifluoromethyl)phenyl)ethyl)-1H-pyrazolo[4,3-d]pyrimidin-7(6H)-one To a solution of 1-(2-(benzyloxy)ethyl)-5-methyl-3-(1-(4-(trifluoromethyl)phenyl)vinyl)-1H-pyrazolo[4,3-d]pyrimidin-7(6H)-one (98 mg, 0.22 mmol) in EtOH (8 mL) at RT under $N_2$ was added 10% Pd/C (69 mg, 0.065 mmol) in one portion. The mixture was evacuated, filled with $H_2$, and was stirred under a $H_2$ balloon for 2 h. The mixture was purged to $N_2$, filtered thru a pad of Celite™, and the pad was washed with EtOH. The resulting filtrate was concentrated under reduced pressure and the resultant residue was purified by reverse-phase HPLC chromatography (SureFire C18 column, 30-90% ACN in water (0.05% TFA)) to afford the racemic title compound as a solid. The enantiopure title compounds were obtained by chiral SFC chromatography (IA column, 10% IPA (0.2% DEA)/$CO_2$). The faster-eluting enantiomer of the title compound (Example 3) was obtained as a solid. $^1$H NMR (CDCl$_3$, 500 MHz) δ: 7.59 (m, 4H), 4.79 (m, 2H), 4.63 (m, 1H), 4.11 (m, 2H), 3.01 (br s, 1H), 2.41 (s, 3H), 1.81 (d, J=7.4 Hz, 3H). MS=366.9 $(M+H)^+$. The slower-eluting enantiomer of the title compound (Example 4) as a solid. $^1$H NMR (CDCl$_3$, 500 MHz) δ: 7.59 (m, 4H), 4.79 (m, 2H), 4.63 (m, 1H), 4.11 (m, 2H), 3.01 (br s, 1H), 2.41 (s, 3H), 1.81 (d, J=7.4 Hz, 3H). MS=366.9 $(M+H)^+$.

TABLE 1

The following compounds were prepared using procedures similar to those described in Examples 3 and 4 using appropriate starting materials. Racemic products were separated using chiral columns specified in the table. For those pairs of enantiomers, the faster-eluting isomer is always listed first in this table.

| Example # | Structure | IUPAC Name | Exact Mass [M + H]+ | Chiral column |
| --- | --- | --- | --- | --- |
| 5 | 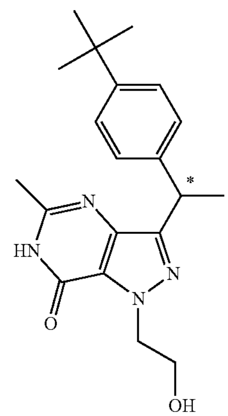 [SMILES: Cc1nc2c(C(C)c3ccc(C(C)(C)C)cc3)nn(CCO)c2c(=O)[nH]1] | (R)- or (S)-3-(1-(4-(tert-Butyl)phenyl)ethyl)-1-(2-hydroxyethyl)-5-methyl-1,6-dihydro-7H-pyrazolo[4,3-d]pyrimidin-7-one | Calc'd 355.2, found 355.1 | Chiralpak IA |
| 6 | 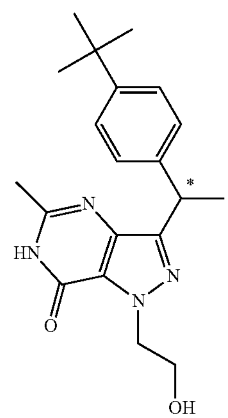 [SMILES: Cc1nc2c(C(C)c3ccc(C(C)(C)C)cc3)nn(CCO)c2c(=O)[nH]1] | (S)- or (R)-3-(1-(4-(tert-Butyl)phenyl)ethyl)-1-(2-hydroxyethyl)-5-methyl-1,6-dihydro-7H-pyrazolo[4,3-d]pyrimidin-7-one | Calc'd 355.2, found 355.1 | Chiralpak IA |
| 7 | 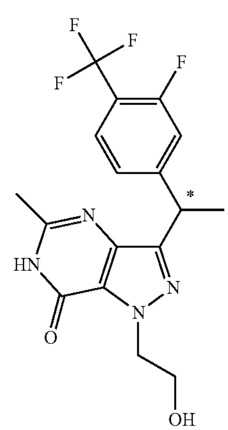 [SMILES: Cc1nc2c(C(C)c3ccc(C(F)(F)F)c(F)c3)nn(CCO)c2c(=O)[nH]1] | (R)- or (S)-3-(1-(3-Fluoro-4-(trifluoromethyl)phenyl)ethyl)-1-(2-hydroxyethyl)-5-methyl-1,6-dihydro-7H-pyrazolo[4,3-d]pyrimidin-7-one | Calc'd 385.1, found 385.0 | Chiralpak IA |

TABLE 1-continued

The following compounds were prepared using procedures similar to those described in Examples 3 and 4 using appropriate starting materials. Racemic products were separated using chiral columns specified in the table. For those pairs of enantiomers, the faster-eluting isomer is always listed first in this table.

| Example # | Structure | IUPAC Name | Exact Mass [M + H]+ | Chiral column |
|---|---|---|---|---|
| 8 | 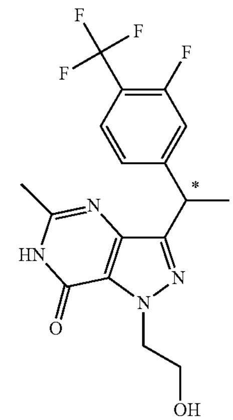 [SMILES: Cc1nc2c(C(C)c3ccc(C(F)(F)F)c(F)c3)nn(CCO)c2c(=O)[nH]1] | (S)- or (R)-3-(1-(3-Fluoro-4-(trifluoromethyl)phenyl)ethyl)-1-(2-hydroxyethyl)-5-methyl-1,6-dihydro-7H-pyrazolo[4,3-d]pyrimidin-7-one | Calc'd 385.1, found 385.0 | Chiralpak IA |
| 9 | 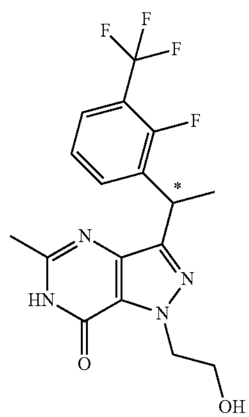 [SMILES: Cc1nc2c(C(C)c3cccc(C(F)(F)F)c3F)nn(CCO)c2c(=O)[nH]1] | (R)- or (S)-3-(1-(2-Fluoro-3-(trifluoromethyl)phenyl)ethyl)-1-(2-hydroxyethyl)-5-methyl-1,6-dihydro-7H-pyrazolo[4,3-d]pyrimidin-7-one | Calc'd 385.1, found 385.0 | Venusil Chiral OD-H |
| 10 | 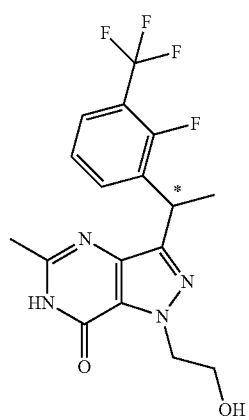 [SMILES: Cc1nc2c(C(C)c3cccc(C(F)(F)F)c3F)nn(CCO)c2c(=O)[nH]1] | (S)- or (R)-3-(1-(2-Fluoro-3-(trifluoromethyl)phenyl)ethyl)-1-(2-hydroxyethyl)-5-methyl-1,6-dihydro-7H-pyrazolo[4,3-d]pyrimidin-7-one | Calc'd 385.1, found 385.0 | Venusil Chiral OD-H |

Examples 11 and 12

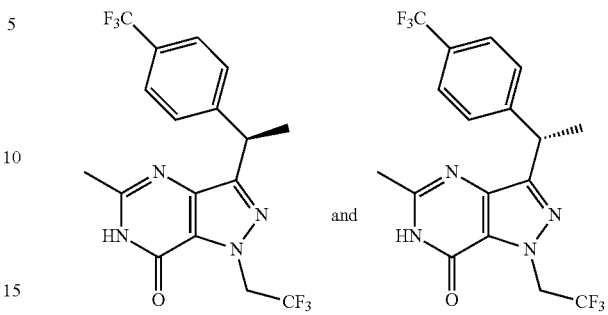

(R)- or (S)-5-Methyl-1-(2,2,2-trifluoroethyl)-3-(1-(4-(trifluoromethyl)phenyl)ethyl)-1H-pyrazolo[4,3-d]pyrimidin-7(6H)-one (Scheme 3)

Step 1. 3-Bromo-5-methyl-1-(2,2,2-trifluoroethyl)-1H-pyrazolo[4,3-d]pyrimidin-7(6H)-one To a suspension of 3-bromo-5-methyl-1H-pyrazolo[4,3-d]pyrimidin-7(6H)-one (100 mg, 0.44 mmol) from step 2 of Examples 1 and 2 in DMF (2 mL) was added $K_2CO_3$ (91 mg, 0.66 mmol) followed by addition of 2-bromo-1,1,1-trifluoroethane (71.1 mg, 0.437 mmol). The mixture was heated to 75° C., stirred for 7 h, and was cooled to RT. The mixture was concentrated under reduced pressure and the residue was purified by reverse-phase HPLC chromatography (Sure-Fire C18 column, 10-90% ACN in water (0.05% TFA)) to afford the title compound as a solid. MS=313.0 $(M+H)^+$.

Step 2. 5-Methyl-1-(2,2,2-trifluoroethyl)-3-(1-(4-(trifluoromethyl)phenyl)vinyl)-1H-pyrazolo[4,3-d]pyrimidin-7(6H)-one To a mixture of 3-bromo-5-methyl-1-(2,2,2-trifluoroethyl)-1H-pyrazolo[4,3-d]pyrimidin-7(6H)-one (60 mg, 0.19 mmol) and 4,4,5,5-tetramethyl-2-(1-(4-(trifluoromethyl)phenyl)vinyl)-1,3,2-dioxaborolane (115 mg, 0.39 mmol), [4-(di-tert-butylphosphino)-N,N-dimethylaniline-2-(2'-aminobiphenyl)]palladium (II) methanesulfonate (1.2 mg, 1.93 μmol) [APhos Pd G3, Aldrich] in NMP (1.8 mL) at RT under $N_2$ was added an aqueous solution of potassium triphosphate (1 M, 0.58 mL, 0.58 mmol). The resulting heterogenous mixture was heated to 80° C. and was stirred at this temperature overnight. The mixture was cooled to RT, filtered, and the filtrate was concentrated under reduced pressure. The residue was purified by reverse-phase HPLC chromatography (SureFire C18 column, 30-90% ACN in water (0.05% TFA)) to afford the title compound as a solid. MS=403.1 $(M+H)^+$.

Step 3. (R)- or (S)-5-Methyl-1-(2,2,2-trifluoroethyl)-3-(1-(4-(trifluoromethyl)phenyl)ethyl)-1H-pyrazolo[4,3-d]pyrimidin-7(6H)-one To a solution of 5-methyl-1-(2,2,2-trifluoroethyl)-3-(1-(4-(trifluoromethyl)phenyl)vinyl)-1H-pyrazolo[4,3-d]pyrimidin-7(6H)-one (70 mg, 0.17 mmol) in EtOH (8 mL) was added 10% Pd—C(55.6 mg, 0.052 mmol) in one portion. The result mixture was evacuated, filled with $H_2$, and was stirred under a $H_2$ balloon for 2 h. The mixture was purged to N₂, filtered thru a pad of Celite™, and the pad was washed with EtOH. The resulting filtrate was concentrated under reduced pressure and the residue was purified by reverse-phase HPLC chromatography (SureFire C18 column, 30-90% ACN in water (0.05% TFA)) to afford the racemic title compound as a solid. The enantiopure title compounds were obtained by chiral SFC chromatography (AD column, 15% IPA (0.2% DEA)/CO₂). The faster-eluting enantiomer of the title compound (Example 11) was obtained as a white solid. ¹H NMR (CDCl₃, 500 MHz) δ: 7.60 (m, 4H), 5.21 (m, 2H), 4.62 (m, 1H), 2.47 (s, 3H), 1.82 (d, J=7.2 Hz, 3H). MS=405.0 (M+H)⁺. The slower-eluting enantiomer of the title compound (Example 12) was obtained as a solid. ¹H NMR (CDCl₃, 500 MHz) δ: 7.60 (m, 4H), 5.21 (m, 2H), 4.62 (m, 1H), 2.47 (s, 3H), 1.82 (d, J=7.2 Hz, 3H). MS=405.0 (M+H)⁺.

Examples 13 and 14

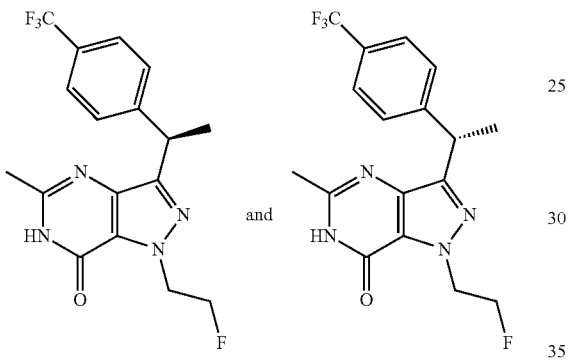

(R)- or (S)-1-(2-Fluoroethyl)-5-methyl-3-(1-(4-(trifluoromethyl)phenyl)ethyl)-1H-pyrazolo[4,3-d]pyrimidin-7(6H)-one (Scheme 4)

To a suspension of 5-methyl-3-(1-(4-(trifluoromethyl)phenyl)ethyl)-1H-pyrazolo[4,3-d]pyrimidin-7(6H)-one (30 mg, 0.093 mmol) from step 4 of Examples 1 and 2 in DMF (1 mL) under N₂ at RT was added K₂CO₃ (11.8 mg, 0.085 mmol) followed by 1-bromo-2-fluoroethane (11.8 mg, 0.093 mmol). The suspension mixture was heated to 75° C., stirred for 1 h, and recooled to RT. Water (0.5 mL) was added the mixture was concentrated under reduced pressure. The residue was purified by reverse-phase HPLC chromatography (SureFire C18 column, 10-90% ACN in water (0.05% TFA)) to afford the racemic title compound as a solid. The enantiopure title compounds were obtained by chiral SFC chromatography (AD column, 10% (2:1 MeOH/CH₃CN)/CO₂). The faster-eluting enantiomer of the title compound (Example 13) was obtained as a solid. ¹H NMR (CDCl₃, 500 MHz) δ: 7.59 (m, 4H), 5.21 (m, 2H), 4.91 (m, 4H), 4.61 (m, 1H), 2.43 (s, 3H), 1.82 (d, J=7.2 Hz, 3H). MS=369.0 (M+H)⁺. The slower-eluting enantiomer of the title compound (Example 14) was obtained as a solid. ¹H NMR (CDCl₃, 500 MHz) δ: 7.59 (m, 4H), 5.21 (m, 2H), 4.91 (m, 4H), 4.61 (m, 1H), 2.43 (s, 3H), 1.82 (d, J=7.2 Hz, 3H). MS=369.0 (M+H)⁺.

Table 2. The following compounds were prepared using procedures similar to those described in Examples 13 and 14 using appropriate starting materials. Racemic products were separated using chiral columns specified in the table. For those pairs of enantiomers, the faster-eluting isomer is always listed first in this table.

| Example # | Structure | IUPAC Name | Exact Mass [M + H]+ | Chiral column |
|---|---|---|---|---|
| 15 | 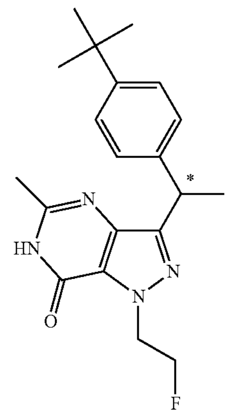 [SMILES: Cc1nc2c(C(C)c3ccc(C(C)(C)C)cc3)nn(CCF)c2c(=O)[nH]1] | (R)- or (S)-3-(1-(4-(tert-Butyl)phenyl)ethyl)-1-(2-fluoroethyl)-5-methyl-1,6-dihydro-7H-pyrazolo[4,3-d]pyrimidin-7-one | Calc'd 357.2, found 357.1 | Lux 5u Cellulose-4 |
| 16 | 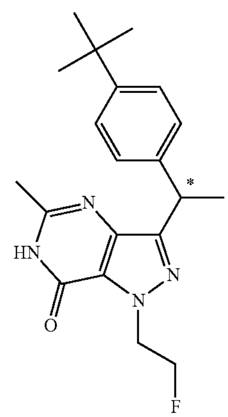 [SMILES: Cc1nc2c(C(C)c3ccc(C(C)(C)C)cc3)nn(CCF)c2c(=O)[nH]1] | (S)- or (R)-3-(1-(4-(tert-Butyl)phenyl)ethyl)-1-(2-fluoroethyl)-5-methyl-1,6-dihydro-7H-pyrazolo[4,3-d]pyrimidin-7-one | Calc'd 357.2, found 357.1 | Lux 5u Cellulose-4 |
| 17 | 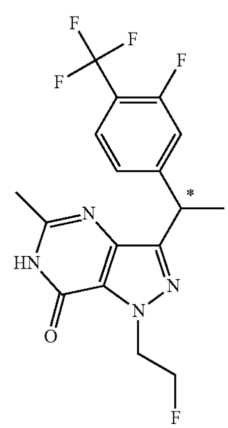 [SMILES: Cc1nc2c(C(C)c3ccc(C(F)(F)F)c(F)c3)nn(CCF)c2c(=O)[nH]1] | (R)- or (S)-3-(1-(3-Fluoro-4-(trifluoromethyl)phenyl)ethyl)-1-(2-fluoroethyl)-5-methyl-1,6-dihydro-7H-pyrazolo[4,3-d]pyrimidin-7-one | Calc'd 387.1, found 387.0 | CHIRALCEL OJ-H |

| Example # | Structure | IUPAC Name | Exact Mass [M + H]+ | Chiral column |
|---|---|---|---|---|
| 18 | 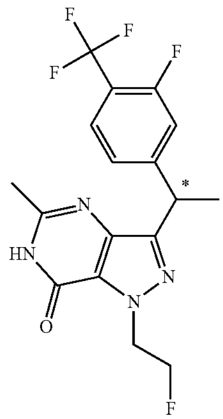 [SMILES: Cc1nc2c(C(C)c3ccc(C(F)(F)F)c(F)c3)nn(CCF)c2c(=O)[nH]1] | (S)- or (R)-3-(1-(3-Fluoro-4-(trifluoromethyl)phenyl)ethyl)-1-(2-fluoroethyl)-5-methyl-1,6-dihydro-7H-pyrazolo[4,3-d]pyrimidin-7-one | Calc'd 387.1, found 387.0 | CHIRALCEL OJ-H |

Examples 19 and 20

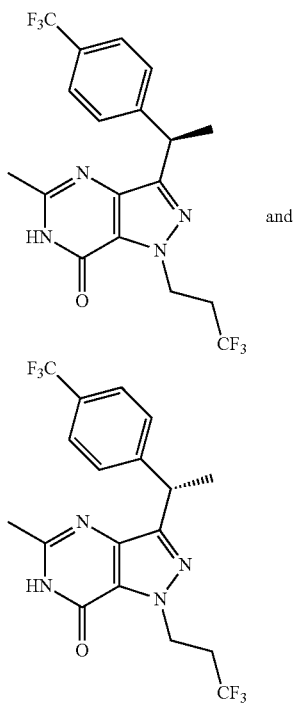

(R)- or (S)-5-Methyl-3-(1-(4-(trifluoromethyl)phenyl)ethyl)-1-(3,3,3-trifluoropropyl)-1H-pyrazolo[4,3-d]pyrimidin-7(6H)-one (Scheme 5)

To a suspension of 5-methyl-3-(1-(4-(trifluoromethyl)phenyl)ethyl)-1H-pyrazolo[4,3-d]pyrimidin-7(6H)-one (40 mg, 0.124 mmol) from step 4 of Examples 1 and 2 in DMF (1 mL) at RT under $N_2$ was added $K_2CO_3$ (17.15 mg, 0.124 mmol) followed by 3-bromo-1,1,1-trifluoropropane (22 mg, 0.124 mmol). The mixture was heated to 75° C., stirred for 1 h, and was cooled to RT. Another portion of 3-bromo-1,1,1-trifluoropropane (22 mg, 0.124 mmol) was added to the mixture which was reheated to 75° C. and stirred for 5 h. The mixture was cooled to RT and was concentrated under reduced pressure. The residue was purified by reverse-phase HPLC chromatography (SureFire C18 column, 30-90% ACN in water (0.05% TFA) to afford the racemic title compound as a solid. The enantiopure title compounds were obtained by chiral SFC chromatography (AD column, 10% (2:1 MeOH/$CH_3CN$)/$CO_2$). The faster-eluting enantiomer of the title compound (Example 19) as a solid. $^1$H NMR (CDCl$_3$, 500 MHz) δ: 7.59 (m, 4H), 4.83 (m, 2H), 4.61 (m, 1H), 2.81 (m, 2H), 2.45 (s, 3H), 1.82 (d, J=7.3 Hz, 3H). MS=418.9 (M+H)$^+$. The slower-eluting enantiomer of the title compound (Example 20) as a solid. $^1$H NMR (CDCl$_3$, 500 MHz) δ: 7.59 (m, 4H), 4.83 (m, 2H), 4.61 (m, 1H), 2.81 (m, 2H), 2.45 (s, 3H), 1.82 (d, J=7.3 Hz, 3H). MS=418.9 (M+H)$^+$.

Examples 21 and 22

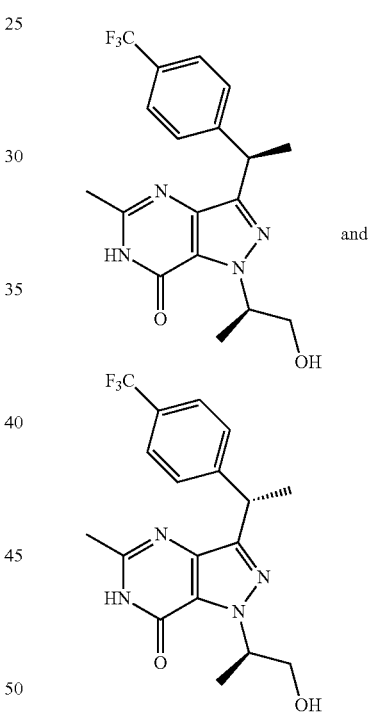

1-((R)-1-Hydroxypropan-2-yl)-5-methyl-3-((S)-1-(4-(trifluoromethyl)phenyl)ethyl)-1,6-dihydro-7H-pyrazolo[4,3-d]pyrimidin-7-one or 1-((R)-1-Hydroxypropan-2-yl)-5-methyl-3-((R)-1-(4-(trifluoromethyl)phenyl)ethyl)-1,6-dihydro-7H-pyrazolo[4,3-d]pyrimidin-7-one (Scheme 6)

Step 1. (R)-1-(1-(Benzyloxy)propan-2-yl)-3-bromo-5-methyl-1H-pyrazolo[4,3-d]pyrimidin-7(6H)-one A suspension of 3-bromo-5-methyl-1H-pyrazolo[4,3-d]pyrimidin-7(6H)-one (200 mg, 0.87 mmol) from step 2 of Examples 1 and 2 in DMF (2 mL) under $N_2$ at RT was added $K_2CO_3$ (181 mg, 1.31 mmol) followed by (S)-((2-bromopropoxy)methyl)benzene (200 mg, 0.873 mmol) from Preparatory Example 1. The mixture was heated to 75° C., stirred for 1 h, and cooled to RT. The solution was filtered and the filtrate was concentrated under reduced pressure. The residue was purified by reverse-phase HPLC chromatography (SureFire C18 column, 10-90% ACN in water (0.05% TFA)) to afford the title compound as a solid. MS=279.1 (M+H)⁺.

Step 2. (R)-1-(1-(Benzyloxy)propan-2-yl)-5-methyl-3-(1-(4-(trifluoromethyl)phenyl)vinyl)-1H-pyrazolo[4,3-d]pyrimidin-7(6H)-one To a suspension of (R)-1-(1-(benzyloxy)propan-2-yl)-3-bromo-5-methyl-1H-pyrazolo[4,3-d]pyrimidin-7(6H)-one (100 mg, 0.265 mmol), 4,4,5,5-tetramethyl-2-(1-(4-(trifluoromethyl)phenyl)vinyl)-1,3,2-dioxaborolane (158 mg, 0.53 mmol), and [4-(di-tert-butylphosphino)-N,N-dimethylaniline-2-(2'-aminobiphenyl)]palladium (II) methanesulfonate (1.7 mg, 2.7 μmol) [APhos Pd G3, Aldrich] in NMP (2.4 mL) under N₂ at RT was added solid potassium triphosphate (169 mg, 0.80 mmol). The resulting heterogenous mixture was heated to 80° C., stirred for 12 h, and was cooled to RT. The mixture was filtered and the resulting filtrate was concentrated under reduced pressure. The residue was purified by reverse-phase HPLC chromatography (SureFire C18 column, 30-90% ACN in water (0.05% TFA)) to afford the title compound as a solid. MS=469.1 (M+H)⁺.

Step 3. 1-((R)-1-Hydroxypropan-2-yl)-5-methyl-3-((S)-1-(4-(trifluoromethyl)phenyl)ethyl)-1,6-dihydro-7H-pyrazolo[4,3-d]pyrimidin-7-one or 1-((R)-1-Hydroxypropan-2-yl)-5-methyl-3-((R)-1-(4-(trifluoromethyl)phenyl)ethyl)-1,6-dihydro-7H-pyrazolo[4,3-d]pyrimidin-7-one The title compound was prepared from (R)-1-(1-(benzyloxy)propan-2-yl)-5-methyl-3-(1-(4-(trifluoromethyl)phenyl)vinyl)-1H-pyrazolo[4,3-d]pyrimidin-7(6H)-one using the procedure set forth in step 4 of Examples 1 and 2 to afford a solid as a mixture of diastereomers. The diastereomerically pure title compounds were obtained by chiral SFC chromatography (OD-H column, 30% MeOH (0.2% DEA)/CO₂). The faster-eluting diastereomer of the title compound (Example 21) as a solid. ¹H NMR (CDCl₃, 500 MHz) δ: 9.50 (br s, 1H), 7.56 (m, 4H), 5.32 (m, 1H), 4.66 (q, J=7.4 Hz, 1H), 4.06 (m, 1H), 4.00 (m, 1H), 2.94 (q, J=4.7 Hz, 1H), 2.48 (s, 3H), 1.81 (d, J=7.3 Hz, 3H), 1.58 (d, J=7.0 Hz, 3H). MS=381.1 (M+H)⁺. The slower-eluting diastereomer of the title compound (Example 22) as a solid. ¹H NMR (CDCl₃, 500 MHz) δ: 10.10 (br s, 1H), 7.56 (m, 4H), 5.31 (m, 1H), 4.66 (m, 1H), 4.06 (m, 1H), 3.98 (m, 1H), 2.97 (m, 1H), 2.48 (s, 3H), 1.82 (d, J=7.3 Hz, 3H), 1.59 (d, J=7.0 Hz, 3H). MS=381.1 (M+H)⁺.

Examples 23 and 24

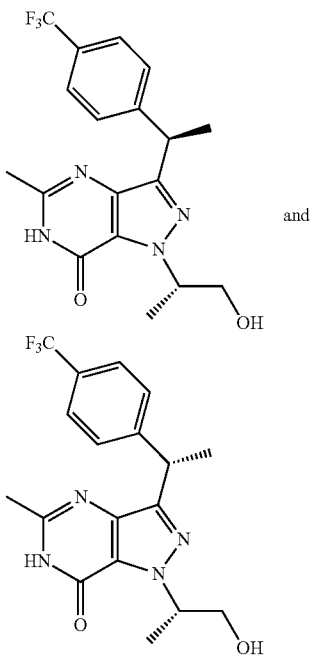

1-((S)-1-Hydroxypropan-2-yl)-5-methyl-3-((S)-1-(4-(trifluoromethyl)phenyl)ethyl)-1,6-dihydro-7H-pyrazolo[4,3-d]pyrimidin-7-one or 1-((S)-1-Hydroxypropan-2-yl)-5-methyl-3-((R)-1-(4-(trifluoromethyl)phenyl)ethyl)-1,6-dihydro-7H-pyrazolo[4,3-d]pyrimidin-7-one (Scheme 7)

Step 1. (S)-1-(1-(Benzyloxy)propan-2-yl)-3-bromo-5-methyl-1H-pyrazolo[4,3-d]pyrimidin-7(6H)-one The title compound was prepared from 3-bromo-5-methyl-1H-pyrazolo[4,3-d]pyrimidin-7(6H)-one from step 2 of Examples 1 and 2 and (R)-((2-bromopropoxy)methyl)benzene from Preparatory Example 2 using the procedure set forth in step 1 of Examples 11 and 12 to afford a solid. MS=279.1 (M+H)⁺.

Step 2. 1 (S)-1-(1-(Benzyloxy)propan-2-yl)-5-methyl-3-(1-(4-(trifluoromethyl)phenyl)vinyl)-1H-pyrazolo[4,3-d]pyrimidin-7(6H)-one The title compound was prepared from (S)-1-(1-(benzyloxy)propan-2-yl)-3-bromo-5-methyl-1H-pyrazolo[4,3-d]pyrimidin-7(6H)-one using the procedure set forth in step 2 of Examples 21 and 22 to afford a solid. MS=469.1 (M+H)⁺.

Step 3. 1-((S)-1-Hydroxypropan-2-yl)-5-methyl-3-((S)-1-(4-(trifluoromethyl)phenyl)ethyl)-1,6-dihydro-7H-pyrazolo[4,3-d]pyrimidin-7-one or 1-((S)-1-Hydroxypropan-2-yl)-5-methyl-3-((R)-1-(4-(trifluoromethyl)phenyl)ethyl)-1,6-dihydro-7H-pyrazolo[4,3-d]pyrimidin-7-one The title compound was prepared from (R)-1-(1-(benzyloxy)propan-2-yl)-5-methyl-3-(1-(4-(trifluoromethyl)phenyl)vinyl)-1H-pyrazolo[4,3-d]pyrimidin-7(6H)-one using the procedure set forth in step 4 of Examples 1 and 2 to afford a solid as a mixture of diastereomers. The diastereomerically pure title compounds were obtained by chiral SFC chromatography (OD-H column, 30% MeOH (0.2% DEA)/$CO_2$). The faster-eluting diastereomer of the title compound (Example 23) was obtained as a solid. $^1$H NMR ($CDCl_3$, 500 MHz) δ: 7.56 (m, 4H), 5.30 (m, 1H), 4.66 (q, J=7.3 Hz, 1H), 4.05 (dd, J=2.5, 11.8 Hz, 1H), 3.98 (dd, J=6.6, 11.8 Hz, 1H), 2.44 (s, 3H), 1.82 (d, J=7.3 Hz, 3H), 1.60 (d, J=6.8 Hz, 3H). MS=381.1 (M+H)$^+$. The slower-eluting enantiomer of the title compound (Example 24) was obtained as a solid. $^1$H NMR ($CDCl_3$, 500 MHz) δ: 7.56 (m, 4H), 5.33 (m, 1H), 4.65 (m, 1H), 4.05 (m, 21), 3.99 (m, 1H), 2.43 (s, 3H), 1.81 (d, J=7.3 Hz, 3H), 1.59 (d, J=6.8 Hz, 3H). MS=381.1 (M+H)$^+$.

Example 25

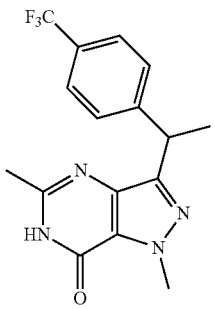 [SMILES: Cc1nc2c(C(C)c3ccc(C(F)(F)F)cc3)nn(C)c2c(=O)[nH]1]

1,5-Dimethyl-3-(1-(4-(trifluoromethyl)phenyl) ethyl)-1,6-dihydro-7H-pyrazolo[4,3-d]pyrimidin-7-one (Scheme 8)

Step 1. 1,5-Dimethyl-1,6-dihydro-7H-pyrazolo[4,3-d]pyrimidin-7-one

The title compound was prepared from ethyl 4-amino-1-methyl-1H-pyrazole-3-carboxylate and benzyl ethanimidothioate hydrochloride using the procedure set forth in step 1 of Examples 1 and 2 to afford a solid. MS=165.1 (M+H)$^+$.

Step 2. 3-Bromo-1,5-dimethyl-1,6-dihydro-7H-pyrazolo[4,3-d]pyrimidin-7-one

The title compound was prepared from 1,5-dimethyl-1,6-dihydro-7H-pyrazolo[4,3-d]pyrimidin-7-one using the procedure set forth in step 2 of Examples 1 and 2 to afford a solid. MS=243.0/245.0 (M+H)$^+$.

Step 3. 1,5-Dimethyl-3-(1-(4-(trifluoromethyl)phenyl)vinyl)-1,6-dihydro-7H-pyrazolo[4,3-d]pyrimidin-7-one The title compound was prepared from 3-bromo-1,5-dimethyl-1,6-dihydro-7H-pyrazolo[4,3-d]pyrimidin-7-one and 4,4,5,5-tetramethyl-2-(1-(4-(trifluoromethyl)phenyl)vinyl)-1,3,2-dioxaborolane using the procedure set forth in step 3 of Examples 1 and 2 to afford a solid. MS=335.1 (M+H)$^+$.

Step 4: 1,5-Dimethyl-3-(1-(4-(trifluoromethyl)phenyl)ethyl)-1,6-dihydro-7H-pyrazolo[4,3-d]pyrimidin-7-one The title compound was prepared from 1,5-dimethyl-3-(1-(4-(trifluoromethyl)phenyl)vinyl)-1,6-dihydro-7H-pyrazolo[4,3-d]pyrimidin-7-one using the procedure set forth in step 4 of Examples 1 and 2 to afford the title compound (Example 25) as a solid $^1$H NMR ($CDCl_3$, 500 MHz) δ: 7.56 (m, 4H), 4.66 (m, 1H), 4.28 (s, 3H), 2.54 (s, 3H), 1.81 (d, J=7.5 Hz, 3H). MS=337.1 (M+H)$^+$.

Examples 26 and 27

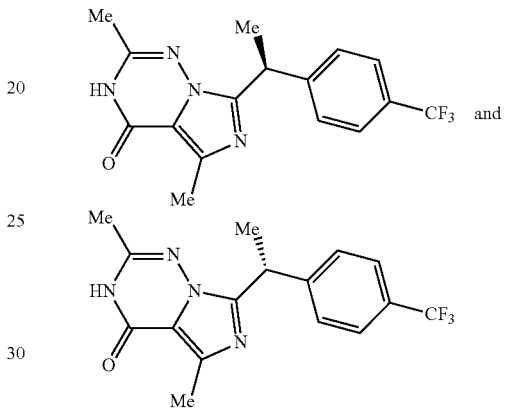

(R)- and (S)-2,5-Dimethyl-7-(1-(4-(trifluoromethyl)phenyl)ethyl)imidazo[5,1-f][1,2,4]triazin-4(3H)-one (Scheme 1)

Step 1. 3-Benzamido-1-methoxy-1-oxobut-2-en-2-yl methyl oxalate

Methyl 2-chloro-2-oxoacetate (1.268 g, 10.35 mmol) was added dropwise to a solution of 2-benzamidopropanoic acid (1 g, 5.18 mmol), pyridine (1.228 g, 15.53 mmol) and 4-N,N-dimethylaminopyridine (0.063 g, 0.518 mmol) in THF (5 mL). The reaction mixture was refluxed for 4 hours, cooled to RT, diluted with water (50 mL) and extracted with ethyl acetate (3×50 mL). The organic layers were combined and washed with brine (2×100 mL). The combined organic extracts were dried over anhydrous sodium sulfate and filtered. The filtrate was concentrated under vacuum. This resulted in the title compound as yellow oil which was used directly in the next step. LCMS (M+1)=322.2.

Step 2. Ethyl 3-benzamido-2-oxobutanoate

To a suspension of 3-benzamido-1-methoxy-1-oxobut-2-en-2-yl methyl oxalate (1.2 g, 3.74 mmol) in ethanol (50 mL) was added a solution of sodium ethoxide in ethanol until a clear yellow solution resulted. This mixture was stirred for an additional 30 minutes. The ethanol was then removed in vacuo to give a yellow oil. The residue was purified by silica gel chromatography (50% ethyl acetate in petroleum ether) to provide the title compound as a yellow oil. LCMS (M+1)=250.2.

Step 3. N-(1-(3-methyl-5-oxo-4,5-dihydro-1,2,4-triazin-6-yl)ethyl)benzamide

To an ice-cold solution of acetamidine hydrochloride (352 mg, 3.72 mmol) in ethanol (10 mL) was slowly added a solution of hydrazine hydrate (161 mg, 3.21 mmol) in ethanol (5 mL). After completion of the addition stirring was continued at RT for 10 minutes. A solution of ethyl 3-benzamido-2-oxobutanoate (800 mg, 3.21 mmol) in ethanol (10 mL) was then added and the mixture was heated at 65°-70° C. with stirring for 20 h. Then the mixture was cooled to RT and the precipitated ammonium chloride was filtered. The filtrate was concentrated and the residue was purified by silica gel chromatography (20:1 $CH_2Cl_2$:MeOH) to furnish the title compound as a yellow oil. LCMS (M+1)=259.2.

Step 4. 6-(1-Aminoethyl)-3-methyl-1,2,4-triazin-5(4H)-one

N-(1-(3-Methyl-5-oxo-4,5-dihydro-1,2,4-triazin-6-yl)ethyl)benzamide (800 mg, 3.10 mmol) in 6 N aqueous HCl solution (15 mL) was heated at 110° C. for 16 h. Then the mixture was cooled to RT and extracted with ethyl acetate. The aqueous layer was evaporated to dryness to furnish the title compound as a yellow solid. LCMS (M+1)=155.2.

Step 5. N-(1-(3-methyl-5-oxo-4,5-dihydro-1,2,4-triazin-6-yl)ethyl)-2-(4-(trifluoromethyl)phenyl)propanamide To a solution of 2-(4-(trifluoromethyl)phenyl)propanoic acid (354 mg, 1.622 mmol) in DMF (5 mL) was added 6-(1-aminoethyl)-3-methyl-1,2,4-triazin-5(4H)-one (250 mg, 1.622 mmol), HATU (1233 mg, 3.24 mmol) and DIEA (0.850 ml, 4.86 mmol). The resulting mixture was stirred for 16 h at RT. Then the reaction mixture was diluted with water (50 mL) and extracted with ethyl acetate (3×100 mL). The combined organic extracts were washed with brine (3×200 mL), dried over anhydrous sodium sulfate, and filtered. The filtrate was concentrated under vacuum to furnish the title compound as a yellow solid. LCMS (M+1)=355.3.

Step 6. (R)- and (S)-2,5-Dimethyl-7-(1-(4-(trifluoromethyl)phenyl)ethyl)imidazo[5,1-f][1,2,4]triazin-4(3H)-one To the solution of N-(1-(5-oxo-4,5-dihydro-1,2,4-triazin-6-yl)ethyl)-2-(4-(trifluoromethyl)phenyl)propanamide (200 mg, 0.588 mmol) in 1,2-dichloroethane (24 mL) was added phosphoryl trichloride (3.0 mL, 0.588 mmol). The resulting mixture was refluxed for 2 h with stirring. The resulting mixture was stirred at 85° C. for 2 h. Then the reaction mixture was cooled to RT, diluted with saturated aqueous $NaHCO_3$ solution (100 mL) and extracted with ethyl acetate (3×50 mL). The combined organic extracts were washed with brine (3×100 mL), dried over anhydrous sodium sulfate and filtered. The filtrate was concentrated under vacuum. The crude product was purified by preparative HPLC (Sunfire Shield C-18 column; 38-44% acetonitrile in water+ 0.05% $NH_4HCO_3$) to furnish the racemic title compound as an off-white solid. The racemate was then resolved by chiral chromatography (Chiralpak IA column; isopropanol in hexane) to furnish the enantiopure title compounds. The faster-eluting enantiomer of the title compound (Example 26): $^1$H NMR (300 MHz, $CD_3OD$) δ: 7.54 (d, J=8.1 Hz, 2H), 7.44 (d, J=8.1 Hz, 2H), 4.77 (q, J=7.5 Hz, 1H), 2.53 (s, 3H), 2.19 (s, 3H), 1.71 (d, J=7.5 Hz, 3H). LCMS (M+1)=337.1.

The slower-eluting enantiomer of the title compound (Example 27): $^1$H NMR (300 MHz, $CD_3OD$) δ: 7.53 (d, J=8.1 Hz, 2H), 7.44 (d, J=8.1 Hz, 2H), 4.78 (q, J=7.2 Hz, 1H), 2.52 (s, 3H), 2.19 (s, 3H), 1.71 (d, J=7.2 Hz, 3H). LCMS (M+1)=337.1.

Examples 28 and 29

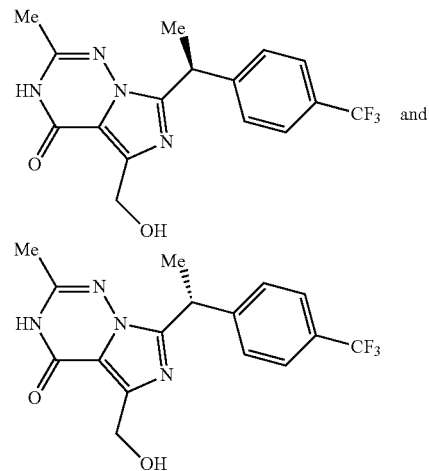

(R)- and (S)-5-(Hydroxymethyl)-2-methyl-7-(1-(4-(trifluoromethyl)phenyl)ethyl)imidazo[5,1-f][1,2,4]triazin-4(3H)-one (Scheme 2)

Step 1. Dimethyl 1-amino-1H-imidazole-4,5-dicarboxylate

Dimethyl 1H-imidazole-4,5-dicarboxylate (3 g, 16.29 mmol), (aminooxy)diphenylphosphine oxide (4.18 g, 17.92 mmol), and sodium carbonate (3.45 g, 32.6 mmol) were combined in dioxane (20 mL) and Water (10 mL) and stirred at RT overnight. Water was added to the reaction and the product was extracted with ethyl acetate (3×150 mL). The extracts were combined, dried over $Na_2SO_4$, filtered, and concentrated to furnish the title compound. LCMS (M+1)= 199.9.

Step 2. Methyl 2-methyl-4-oxo-1,4-dihydroimidazo[5,1-f][1,2,4]triazine-5-carboxylate HCl gas was bubbled through a solution of dimethyl 1-amino-1H-imidazole-4,5-dicarboxylate (3.24 g, 16.27 mmol) in acetonitrile (20 mL) for 10 minutes. The reaction was then stirred for 3 h at RT. The mixture was concentrated and the solid was dissolved in 100 mL MeOH and treated with 1 N aqueous sodium hydroxide solution (48.8 ml, 48.8 mmol). This mixture was stirred at 40° C. overnight. The methanol was removed and the pH was adjusted to 1 with 6N HCl. The resulting precipitate was filtered off and washed with water and then dried under air to provide the title compound and 2-methyl-4-oxo-1,4-dihydroimidazo[5,1-f][1,2,4]triazine-5-carboxylic acid as a mixture. Thionyl chloride (1.402 ml, 19.21 mmol) was added to MeOH (50 ml) cooled to 0° C. The reaction was stirred at 0 C for 30 minutes and then methyl 2-methyl-4-oxo-3,4-dihydroimidazo[5,1-f][1,2,4]triazine-5-carboxylate (2 g, 9.61 mmol)/2-methyl-4-oxo-3,4-dihydroimidazo[5,1-f][1,2,4]triazine-5- carboxylic acid (1.865 g, 9.61 mmol) was added directly to the mixture. The reaction was then warmed to 60° C. overnight. The reaction was cooled to RT and the solvent was removed. The residue was dissolved in ethyl acetate and washed with saturated aqueous $NaHCO_3$ solution. The organic extract was dried over $Na_2SO_4$, filtered, and concentrated to furnish the title compound. LCMS (M+1)=208.9.

Step 3. Butyl 2-methyl-4-oxo-3,4-dihydroimidazo [5,1-f][1,2,4]triazine-5-carboxylate To a 100-mL round-bottom flask was added methyl 2-methyl-4-oxo-3,4-dihydroimidazo[5,1-f][1,2,4]triazine-5-carboxylate (4.0 g, 19.21 mmol), n-butanol (40 mL) and $H_2SO_4$ (0.031 mL, 0.576 mmol). The reaction mixture was degassed with nitrogen 3 times and stirred under an atmosphere of nitrogen for 16 h at 100° C. The reaction mixture was cooled to RT and 20 mL of DCM were added. The resulting solid was filtered, washed with petroleum ether (2×20 mL), and dried to furnish the title compound as a colorless solid. LCMS (M+1)=260.0.

Step 4. Butyl 7-bromo-2-methyl-4-oxo-3,4-dihydroimidazo[5,1-f][1,2,4]triazine-5-carboxylate Into a 100-mL round-bottom flask, bromine (2.306 mL, 44.8 mmol) and butyl 2-methyl-4-oxo-3,4-dihydroimidazo [5,1-f][1,2,4]triazine-5-carboxylate (3.2 g, 12.79 mmol) were combined in DMF (63 mL). The reaction mixture was stirred for 16 h at RT to give a brown solution. The resulting mixture was diluted with sodium sulfite (saturated, 100 mL) and extracted with ethyl acetate (3×100 mL). The combined organic extracts were washed with water (3×100 mL), dried over anhydrous sodium sulfate and filtered. The filtrate was concentrated under vacuum to furnish the title compound as a colorless solid. LCMS (M+1)=328.9 and 330.9.

Step 5. Butyl 7-(1-ethoxyvinyl)-2-methyl-4-oxo-3, 4-dihydroimidazo[5,1-f][1,2,4]triazine-5-carboxylate Into a 20-mL sealed tube, butyl 7-bromo-2-methyl-4-oxo-3,4-dihydroimidazo[5,1-f][1,2,4]triazine-5-carboxylate (700 mg, 2.127 mmol), tributyl(1-ethoxyvinyl)stannane (845 mg, 2.339 mmol), $Pd(PPh_3)_4$ (246 mg, 0.213 mmol) and toluene (8 mL) were added. The reaction mixture was degassed with nitrogen 3 times and stirred under an atmosphere of nitrogen for 4 h at 120° C. The reaction mixture was cooled to RT, diluted with saturated brine (40 mL) and extracted with ethyl acetate (3×40 mL). The combined organic extracts were dried over anhydrous sodium sulfate and filtered. The filtrate was concentrated under vacuum. The residue was purified by silica gel chromatography (70% ethyl acetate in hexanes) to furnish the title compound as a yellow solid. LCMS (M+1)=321.1.

Step 6. Butyl 7-acetyl-2-methyl-4-oxo-3,4-dihydroimidazo[5,1-f][1,2,4]triazine-5-carboxylate To a solution of butyl 7-(1-ethoxyvinyl)-2-methyl-4-oxo-3,4-dihydroimidazo[5,1-f][1,2,4]triazine-5-carboxylate (1.8 g, 5.62 mmol) in THF (8 mL) cooled to 0° C. was added 3N aqueous HCl (16.86 mL, 50.6 mmol) dropwise. The reaction mixture was stirred for 1 h at RT to give a colorless solution. The resulting mixture was diluted with brine (40 mL) and extracted with ethyl acetate (3×60 mL). The combined organic extracts were dried over anhydrous sodium sulfate and filtered. The filtrate was concentrated under vacuum. The residue was purified by silica gel chromatography (20:1 DCM:MeOH) to furnish the title compound as a colorless solid. LCMS (M+1)=293.0.

Step 7. Butyl 7-(1-hydroxy-1-(4-(trifluoromethyl) phenyl)ethyl)-2-methyl-4-oxo-3,4-dihydroimidazo[5, 1-f][1,2,4]triazine-5-carboxylate To a solution of 1-bromo-4-(trifluoromethyl)benzene (577 mg, 2.57 mmol) in THF (20 mL) cooled to −78° C. was added n-butyllithium (1.283 ml (2M in hexanes), 2.57 mmol) under nitrogen. The resulting mixture was stirred for 1 h at −78° C. To the reaction mixture was added a solution of butyl 7-acetyl-2-methyl-4-oxo-3,4-dihydroimidazo[5,1-f] [1,2,4]triazine-5-carboxylate (300 mg, 1.026 mmol) in THF (20 mL). The resulting mixture was warmed to RT and stirred for 16 h at this temperature. Then the reaction mixture was diluted with $H_2O$ (20 mL) and extracted with ethyl acetate (3×20 mL). The combined organic extracts were washed with brine (3×50 mL), dried over anhydrous sodium sulfate, and filtered, and concentrated under vacuum. The residue was purified by silica gel chromatography (75% ethyl acetate in hexanes) to furnish the title compound as a white solid. LCMS (M+1)=439.0.

Step 8. Butyl 2-methyl-4-oxo-7-(1-(4-(trifluoromethyl)phenyl)vinyl)-3,4-dihydroimidazo[5,1-f][1,2,4] triazine-5-carboxylate To the suspension of butyl 7-(1-hydroxy-1-(4-(trifluoromethyl)phenyl)ethyl)-2-methyl-4-oxo-3,4-dihydroimidazo[5, 1-f][1,2,4]triazine-5-carboxylate (150 mg, 0.342 mmol) in toluene (7 mL) was added Burgess reagent (245 mg, 1.026 mmol) at RT. The resulting mixture was stirred for 16 h at 110° C. The reaction mixture was cooled and then purified by silica gel column chromatography (50% ethyl acetate in hexanes) to furnish the title compound as a white solid. LCMS (M+1)=421.3.

Step 9. Butyl 2-methyl-4-oxo-7-(1-(4-(trifluoromethyl)phenyl)ethyl)-3,4-dihydroimidazo[5,1-f][1,2,4] triazine-5-carboxylate Butyl 2-methyl-4-oxo-7-(1-(4-(trifluoromethyl)phenyl) vinyl)-3,4-dihydroimidazo[5,1-f][1,2,4]triazine-5-carboxylate (250 mg, 0.595 mmol) was dissolved in ethanol (1.5 ml) and the solution was degassed 3 times. Then Pd—C(190 mg, 0.178 mmol) was added to the solution. The mixture was then stirred under an atmosphere of hydrogen at 25° C. for 2 h. The solid was filtered and the filtrate was concentrated to provide the title compound as a white solid. LCMS (M+1)=423.1.

Step 10. (R)- and (S)-5-(Hydroxymethyl)-2-methyl-7-(1-(4-(trifluoromethyl)phenyl)-ethyl)imidazo[5,1-f][1,2,4]triazin-4(3H)-one To a solution of butyl 2-methyl-4-oxo-7-(1-(4-(trifluoromethyl)phenyl)ethyl)-3,4-dihydroimidazo[5,1-f][1,2,4] triazine-5-carboxylate (210 mg, 0.497 mmol) in THF (10 ml) was added $NaBH_4$ (56.4 mg, 1.491 mmol). The resulting mixture was stirred for 16 h at 40° C. The reaction mixture was cooled to RT, diluted with $NH_4Cl$ (50 mL), and the product was extracted with ethyl acetate (3×50 mL). The combined organic extracts were washed with brine (3×100 mL), dried over anhydrous sodium sulfate, filtered, and concentrated. The residue was purified by silica gel chromatography (15:1 DCM:MeOH) to furnish the racemic title compound as a white solid. The racemate was then resolved by chiral chromatography (Chiralpak IA column; 27% methanol in $CO_2$+0.2% $NH_4OH$) to furnish the enantiopure title compounds. The faster-eluting enantiomer of the title compound (Example 28): $^1$H NMR (500 MHz, CDCl$_3$) δ: 9.55 (s, 1H), 7.57 (d, J=8.5 Hz, 2H), 7.52 (d, J=8.5 Hz, 2H), 4.99 (s, 2H), 4.81 (q, J=7.0 Hz, 1H), 2.38 (s, 3H), 1.83 (d, J=7.0 Hz, 3H). LCMS (M+1)=352.9. The slower-eluting enantiomer of the title compound (Example 29): $^1$H NMR (500 MHz, CDCl$_3$) δ: 8.91 (s, 1H), 7.57 (d, J=8.5 Hz, 2H), 7.52 (d, J=8.5 Hz, 2H), 4.98 (s, 2H), 4.79 (q, J=7.0 Hz, 1H), 2.37 (s, 3H), 1.81 (d, J=7.0 Hz, 3H). LCMS (M+1)=352.9.

TABLE 3

The following compounds were prepared using procedures similar to those described in Examples 28 and 29 using appropriate starting materials. Racemic products were separated using chiral columns specified in the table. For those pairs of enantiomers, the faster-eluting isomer is always listed first in this table.

| Example No. | Structure | IUPAC Name | Exact Mass [M + H]$^+$ | Chiral column |
| --- | --- | --- | --- | --- |
| 30 | 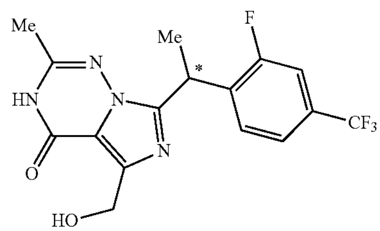 [SMILES: Cc1nn2c(C(C)c3ccc(C(F)(F)F)cc3F)nc(CO)c2c(=O)[nH]1] | (R)- or (S)-7-(1-(2-fluoro-4-(trifluoromethyl)phenyl)ethyl)-5-(hydroxymethyl)-2-methylimidazo[5,1-f][1,2,4]triazin-4(3H)-one | Calc'd 371.3, found 371.2 | Lux Cellulose-4 |
| 31 | 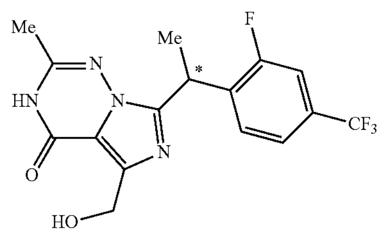 [SMILES: Cc1nn2c(C(C)c3ccc(C(F)(F)F)cc3F)nc(CO)c2c(=O)[nH]1] | (S)- or (R)-7-(1-(2-fluoro-4-(trifluoromethyl)phenyl)ethyl)-5-(hydroxymethyl)-2-methylimidazo[5,1-f][1,2,4]triazin-4(3H)-one | Calc'd 371.3, found 371.2 | Lux Cellulose-4 |
| 32 | 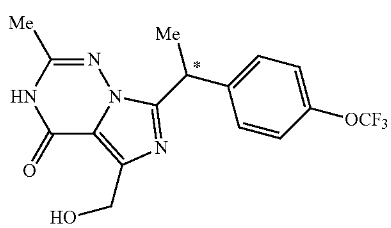 [SMILES: Cc1nn2c(C(C)c3ccc(OC(F)(F)F)cc3)nc(CO)c2c(=O)[nH]1] | (R)- or (S)-5-(hydroxymethyl)-2-methyl-7-(1-(4-(trifluoromethoxy)phenyl)ethyl)imidazo[5,1-f][1,2,4]triazin-4(3H)-one | Calc'd 369.3, found 369.1 | Chiralpak-IA |
| 33 | 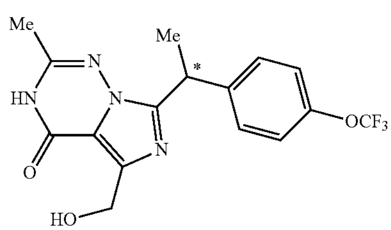 [SMILES: Cc1nn2c(C(C)c3ccc(OC(F)(F)F)cc3)nc(CO)c2c(=O)[nH]1] | (S)- or (R)-5-(hydroxymethyl)-2-methyl-7-(1-(4-(trifluoromethoxy)phenyl)ethyl)imidazo[5,1-f][1,2,4]triazin-4(3H)-one | Calc'd 369.3, found 369.1 | Chiralpak-IA |
| 34 | 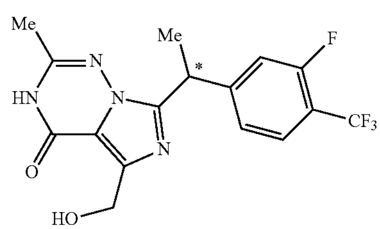 [SMILES: Cc1nn2c(C(C)c3ccc(C(F)(F)F)c(F)c3)nc(CO)c2c(=O)[nH]1] | (R)- or (S)-7-(1-(3-fluoro-4-(trifluoromethyl)phenyl)ethyl)-5-(hydroxymethyl)-2-methylimidazo[5,1-f][1,2,4]triazin-4(3H)-one | Calc'd 371.3, found 371.2 | Chiralpak-IA |

TABLE 3-continued

The following compounds were prepared using procedures similar to those described in Examples 28 and 29 using appropriate starting materials. Racemic products were separated using chiral columns specified in the table. For those pairs of enantiomers, the faster-eluting isomer is always listed first in this table.

| Example No. | Structure | IUPAC Name | Exact Mass [M + H]+ | Chiral column |
|---|---|---|---|---|
| 35 | 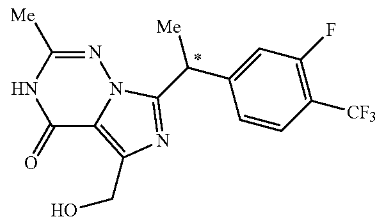 [SMILES: Cc1nn2c(C(C)c3ccc(C(F)(F)F)c(F)c3)nc(CO)c2c(=O)[nH]1] | (S)- or (R)-7-(1-(3-fluoro-4-(trifluoromethyl)phenyl)ethyl)-5-(hydroxymethyl)-2-methylimidazo[5,1-f][1,2,4]triazin-4(3H)-one | Calc'd 371.3, found 371.2 | Chiralpak-IA |
| 36 | 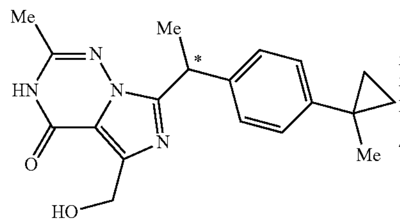 | (R)- or (S)-5-(hydroxymethyl)-2-methyl-7-(1-(4-(1-methylcyclopropyl)phenyl)ethyl)imidazo[5,1-f][1,2,4]triazin-4(3H)-one | Calc'd 339.4, found 339.1 | Lux Cellulose-4 |
| 37 | 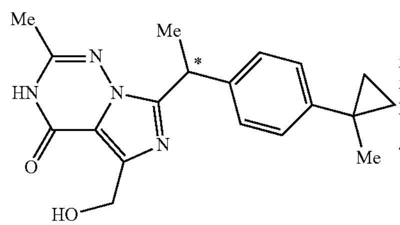 | (S)- or (R)-5-(hydroxymethyl)-2-methyl-7-(1-(4-(1-methylcyclopropyl)phenyl)ethyl)imidazo[5,1-f][1,2,4]triazin-4(3H)-one | Calc'd 339.4, found 339.1 | Lux Cellulose-4 |

Examples 38, 39, and 40

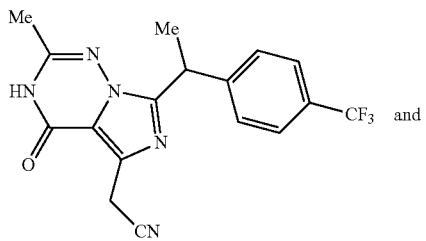

and

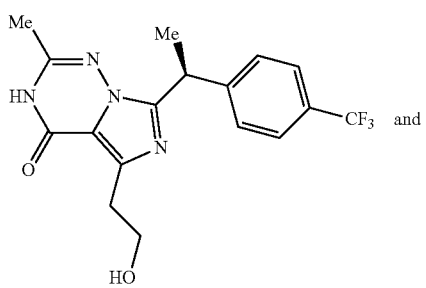

and

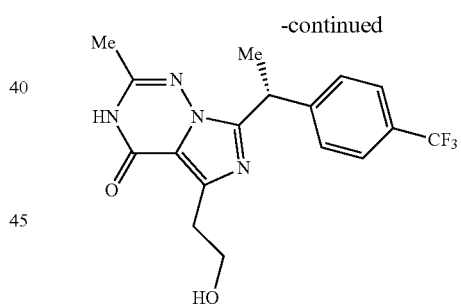

2-(2-Methyl-4-oxo-7-(1-(4-(trifluoromethyl)phenyl)ethyl)-3,4-dihydroimidazo[5,1-f][1,2,4]triazin-5-yl)acetonitrile and (R)- and (S)-5-(2-hydroxyethyl)-2-methyl-7-(1-(4-(trifluoromethyl)phenyl)ethyl)imidazo[5,1-f][1,2,4]triazin-4(3H)-one (Scheme 3)

Step 1. 5-(Chloromethyl)-2-methyl-7-(1-(4-(trifluoromethyl)phenyl)ethyl)imidazo[5,1-f][1,2,4]triazin-4(3H)-one To a solution of 5-(hydroxymethyl)-2-methyl-7-(1-(4-(trifluoromethyl)phenyl)ethyl)imidazo[5,1-f][1,2,4]triazin-4(3H)-one (300 mg, 0.852 mmol) in THF (10 mL) was added sulfurous dichloride (304 mg, 2.55 mmol) and pyridine (0.207 ml, 2.55 mmol). The resulting suspension was stirred for 2 h at RT. The reaction mixture was then diluted with ethyl acetate (20 mL) and washed with brine (3×20 mL). The combined organic layers were dried over anhydrous sodium sulfate, filtered, and concentrated under vacuum. The residue was purified by silica gel chromatography (50% ethyl acetate in hexanes) to furnish the title compound as a white solid. LCMS (M+1)=371.0, 373.0.

Step 2. 2-(2-methyl-4-oxo-7-(1-(4-(trifluoromethyl) phenyl)ethyl)-3,4-dihydroimidazo-[5,1-f][1,2,4]triazin-5-yl)acetonitrile (Example 38)

To a solution of sodium cyanide (174 mg, 3.56 mmol) in DMSO (16 mL) was added a solution of 5-(chloromethyl)-2-methyl-7-(1-(4-(trifluoromethyl)phenyl)ethyl)imidazo[5,1-f][1,2,4]triazin-4(3H)-one (220 mg, 0.593 mmol) in DMSO (1 mL). The resulting mixture was stirred for 1 h at RT. Then the reaction mixture was diluted with water (30 mL) and extracted with ethyl acetate (3×50 mL). The combined organic extracts were washed with brine (3×100 mL), dried over anhydrous sodium sulfate, filtered, and concentrated to furnish the title compound as a white solid. LCMS (M+1)=362.2.

Step 3. methyl 2-(2-methyl-4-oxo-7-(1-(4-(trifluoromethyl)phenyl)ethyl)-3,4-dihydroimidazo[5,1-f][1,2,4]triazin-5-yl)acetate To a solution of HCl in MeOH (10 mL) was added 2-(2-methyl-4-oxo-7-(1-(4-(trifluoromethyl)phenyl)ethyl)-3,4-dihydroimidazo[5,1-f][1,2,4]triazin-5-yl)acetonitrile (110 mg, 0.274 mmol). The resulting solution was stirred at 70° C. for 2 h. Then the reaction mixture was cooled to RT, diluted with NaHCO$_3$ solution (5 mL), and extracted with ethyl acetate (3×10 mL). The combined organic extracts were washed with brine (3×10 mL), dried over anhydrous sodium sulfate, filtered, and concentrated. The residue was purified by silica gel chromatography (25% ethyl acetate in hexanes) to furnish the title compound as a white solid. LCMS (M+1)=395.1.

Step 4. 5-(2-Hydroxyethyl)-2-methyl-7-(1-(4-(trifluoromethyl)phenyl)ethyl)imidazo[5,1-f][1,2,4]triazin-4(3H)-one To a solution of LiBH$_4$ (29.8 mg, 1.369 mmol) in THF (5 mL) was added methyl 2-(2-methyl-4-oxo-7-(1-(4-(trifluoromethyl)phenyl)ethyl)-3,4-dihydroimidazo[5,1-f][1,2,4] triazin-5-yl)acetate (90 mg, 0.228 mmol) at 0° C. The resulting mixture was stirred for 16 h at RT. Then the reaction mixture was quenched with aqueous ammonium chloride solution. The resulting mixture was stirred for another 16 h at RT. Then the reaction mixture was cooled to RT, diluted with NH$_4$Cl solution (100 mL), and extracted with ethyl acetate (3×20 mL). The combined organic extracts were washed with brine (3×20 mL), dried over anhydrous sodium sulfate, filtered, and concentrated. The residue was purified by preparative HPLC (X Bridge C-18 column; 20-40% acetonitrile in water+0.05% NH$_4$HCO$_3$) to furnish the racemic title compound as a white solid after concentration of the product-containing fractions. The racemate was then resolved by chiral chromatography (Chiralpak IC column; 10% ethanol in hexanes) to furnish the enantiopure title compounds. The faster-eluting enantiomer of the title compound (Example 39): $^1$H NMR (400 MHz, CD$_3$OD) δ: 7.64 (d, J=8.0 Hz, 2H), 7.47 (d, J=7.2 Hz, 2H), 5.01 (q, J=7.2 Hz, 1H), 3.89 (t, J=6.4 Hz, 2H), 3.25 (t, J=6.4 Hz, 2H), 2.30 (s, 3H), 1.84 (d, J=7.2 Hz, 3H). LCMS (M+1)=367.2. The slower-eluting enantiomer of the title compound (Example 40): $^1$H NMR (400 MHz, DMSO-d$_6$) δ: 11.67-11.53 (br, 1H), 7.66 (d, J=7.6 Hz, 2H), 7.51 (d, J=7.2 Hz, 2H), 4.73 (q, J=7.2 Hz, 1H), 4.64 (s, 1H), 3.67 (t, J=6.4 Hz, 2H), 3.02 (t, J=6.4 Hz, 2H), 2.16 (s, 3H), 1.64 (d, J=7.2 Hz, 3H). LCMS (M+1)=367.2.

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 µM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 µM concentration for 100% inhibition. Bay 60-7550 was obtained from Axxora via Fisher Scientific (cat# ALX-270-421-M025/cat#NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM $MgCl_2$, 0.05% $NaN_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization($mP$)=1000*($S/So-P/Po$)/($S/So+P/Po$).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1⇒same as this control), the minimum inhibition at the high plateau relative to the "0% Inhibition Control" (Imin, e.g. 0⇒same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% mP - 100\% mP)(Imax - Imin)}{1 + \left[\frac{[Drug]}{(10^{-pK_I}(1 + \frac{[Substrate]}{K_M}))}\right]^{nH}} +$$

$$100\% mP + (0\% mP - 100\% mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1(Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 μL. Solutions of test compounds were prepared in DMSO and serially diluted with DMSO to yield 30 μL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 μM. Many of compounds within the present invention had activity in inhibiting the human PDE2 enzyme in the aforementioned assays, with a Ki of less than about 1 μM, preferably less than or about 0.1 μM. Additional data is provided in the following Examples. Such a result is indicative of the intrinsic activity of the compounds in use as inhibitors of the PDE2 enzyme. In general, one of ordinary skill in the art would appreciate that a substance is considered to be particularly effective for inhibiting PDE2 activity if it has a Ki of less than or about 1 μM, preferably less than or about 0.1 μM. The present invention also includes compounds within the generic scope of the invention which possess activity as inhibitors of other phosphodiesterase enzymes.

In the following tables are representative data for the compounds of formulas I and II as PDE2 inhibitors as determined by the foregoing assays. The PDE2 Ki is a measure of the ability of the test compound to inhibit the action of the PDE2 enzyme.

TABLE 4

PDE2 Ki's

| Example No. | rhesus PDE2 Ki (nM) | human PDE2 Ki (nM) |
| --- | --- | --- |
| 1 | 17.8 | 15.2 |
| 2 | 293 | NA |
| 3 | NA | 64.7 |
| 4 | NA | 1.7 |
| 5 | NA | 125 |
| 6 | NA | 2.7 |
| 7 | NA | 32.1 |
| 8 | NA | 1.1 |
| 9 | NA | 2800 |
| 10 | NA | 206 |
| 11 | 178 | NA |
| 12 | 6.3 | 7.0 |
| 13 | NA | 26.8 |
| 14 | NA | 1.8 |
| 15 | NA | 1.3 |
| 16 | NA | 82.9 |
| 17 | NA | 24.5 |
| 18 | 1.0 | 0.9 |
| 19 | NA | 521 |
| 20 | NA | 323.6 |
| 21 | NA | 239 |
| 22 | NA | 15.6 |
| 23 | NA | 141.9 |
| 24 | NA | 6.7 |
| 25 | 70.3 | 60.9 |
| 26 | 778.8 | NA |
| 27 | 21.0 | 17.2 |
| 28 | NA | 298 |
| 29 | NA | 1.2 |
| 30 | NA | 199.7 |
| 31 | NA | 0.8 |
| 32 | NA | 62.5 |
| 33 | NA | 1.2 |
| 34 | NA | 215.8 |
| 35 | NA | 1.0 |
| 36 | NA | 109.1 |
| 37 | NA | 0.4 |
| 38 | NA | 6.1 |
| 39 | NA | 90.3 |
| 40 | NA | 1.7 |

(NA = Not available)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of structural formulas I and II:

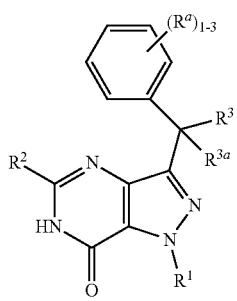

I

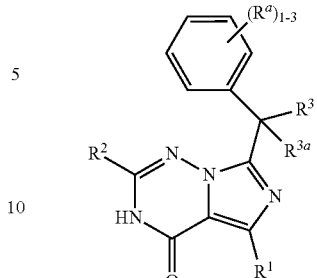

II or a pharmaceutically acceptable salt thereof, wherein:

$R^1$ represents hydrogen, or $C_{1-6}$alkyl, said alkyl optionally substituted with 1 to 3 groups of $R^b$, $R^2$ represents OR, $NR_2$, $C_{1-6}$alkyl, $(CH_2)_{1-4}OR$, $C_{1-4}$haloalkyl, $C(O)C_{6-10}$aryl, $—(CH_2)_nC_{6-10}$aryl, $(CH_2)_nC_{3-10}$heterocyclyl or $(CH_2)_nC_{3-10}$cycloalkyl wherein when $R^2$ is a heterocyclyl it is attached to the pyrazolopyrimidinone or imidazotriazinone ring through a carbon atom, and wherein said alkyl, aryl, heterocyclyl and cycloalkyl are optionally substituted with 1 to 3 groups of $R^a$ $R^3$ and $R^{3a}$ independently represent hydrogen, $C_{1-6}$alkyl, or $C_{3-6}$cycloalkyl, said alkyl, and cycloalkyl, optionally substituted with 1 to 3 groups of $R^a$, or $R^3$ and $R^{3a}$ can combine with the carbon atom to which they are attached to form a $C_{3-6}$ cycloalkyl, or $C_{4-10}$heterocycloalkyl, said alkyl, cycloalkyl, and heterocycloalkyl optionally substituted with 1 to 3 groups of $R^a$, R represents hydrogen, or $C_{1-6}$alkyl, $R^a$ is selected from the group consisting of hydrogen, halo, CN, $SCF_3$, $SF_5$, $C_{1-6}$alkyl, $(CH_2)_nOR$, $(CH_2)_nC_{1-4}$haloalkyl, $O—C_{1-4}$haloalkyl, $C_{3-6}$cycloalkyl, said alkyl and cycloalkyl optionally substituted with 1 to 3 groups of $C_{1-6}$alkyl or halo;

$R^b$ is selected from the group consisting of halo, CN, $C_{1-6}$alkyl, $(CH_2)_nOR$, $(CH_2)_nC_{1-4}$haloalkyl, $O—C_{1-4}$haloalkyl, and n represents 0, 1, 2, 3, or 4.

2. The compound according to claim 1 or a pharmaceutically acceptable salt thereof wherein $R^1$ is $C_{1-6}$alkyl, said alkyl optionally substituted with 1 to 3 groups of $R^b$.

3. The compound according to claim 2 or a pharmaceutically acceptable salt thereof wherein the optionally substituted $C_{1-6}$alkyl of $R^1$ is selected from the group consisting of $CH_3$, $CH_2OH$, $CH_2CH_2OH$, $CH_2CN$, $CH_2CF_3$, $CH_2CH_2F$, $CH_2CH_2CF_3$, $CH_2CHF_2$, $CH(CH_2OH)CH_3$.

4. The compound according to claim 1 or a pharmaceutically acceptable salt thereof wherein $R^2$ is optionally substituted $C_{1-6}$alkyl.

5. The compound according to claim 4 or a pharmaceutically acceptable salt thereof wherein $R^2$ is selected from the group consisting OR, and $NR_2$, $(CH_2)_nCH_3$, $CH(CH_3)_2$, and $C(CH_3)_3$.

6. The compound according to claim 1 or a pharmaceutically acceptable salt thereof wherein $R^3$ and $R^{3a}$ independently represent hydrogen or optionally substituted $C_{1-6}$alkyl.

7. The compound according to claim 6 or a pharmaceutically acceptable salt thereof wherein $R^3$ and $R^{3a}$ independently represent methyl, ethyl, propyl, isopropyl, butyl, $CH_2OH$, $CH_2CH_2OH$, $CH_2CN$, $CH_2CF_3$, $CH_2CH_2F$, $CH_2CH_2CF_3$, $CH_2CHF_2$, or $CH(CH_2OH)CH_3$.

8. The compound according to claim 1 or a pharmaceutically acceptable salt thereof wherein $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$alkyl or halo.

9. The compound according to claim 1 represented by structural formula Ia:

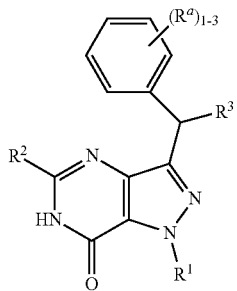

Ia or a pharmaceutically acceptable salt thereof.

10. The compound according to claim 9 or a pharmaceutically acceptable salt thereof wherein $R^1$ is optionally substituted $C_{1-6}$alkyl selected from the group consisting of $CH_3$, $CH_2CH_2OH$, $CH_2CN$, $CH_2CF_3$, $CH_2CH_2F$, $CH_2CH_2CF_3$, $CH(CH_2OH)CH_3$, and $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$ alkyl or halo.

11. The compound according to claim 9 or a pharmaceutically acceptable salt thereof wherein $R^2$ is selected from the group consisting OR, $NR_2$, $(CH_2)_nCH_3$, $CH(CH_3)_2$, and $C(CH_3)_3$.

12. The compound according to claim 1 or a pharmaceutically acceptable salt thereof wherein $R^3$ is selected from the group consisting of methyl, ethyl, propyl, isopropyl, butyl, $CH_2OH$, $CH_2CH_2OH$, $CH_2CN$, $CH_2CF_3$, $CH_2CH_2F$, $CH_2CH_2CF_3$, $CH_2CHF_2$, and $CH(CH_2OH)CH_3$.

13. The compound according to 9 or a pharmaceutically acceptable salt thereof wherein $R^1$ is optionally substituted $C_{1-6}$alkyl selected from the group consisting of $CH_3$, $CH_2CH_2OH$, $CH_2CN$, $CH_2CF_3$, $CH_2CH_2F$, $CH_2CH_2CF_3$, $CH(CH_2OH)CH_3$, $R^2$ and $R^3$ are methyl, and $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$alkyl or halo.

14. The compound of claim 1 of formula II represented by structural formula IIa:

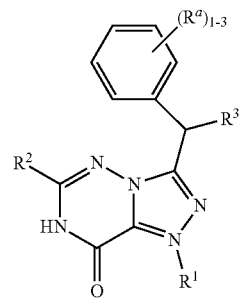

IIa or a pharmaceutically acceptable salt thereof.

15. The compound according to claim 14 or a pharmaceutically acceptable salt thereof wherein $R^1$ is optionally substituted $C_{1-6}$alkyl selected from the group consisting of $CH_3$, $CH_2OH$, $CH_2CH_2OH$, $CH_2CN$, $CH_2CF_3$, $CH_2CH_2F$, $CH_2CH_2CF_3$, $CH(CH_2OH)CH_3$, and $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$ alkyl or halo.

16. The compound according to claim 14 or a pharmaceutically acceptable salt thereof wherein $R^2$ is selected from the group consisting OR, $NR_2$, $(CH_2)_nCH_3$, $CH(CH_3)_2$, and $C(CH_3)_3$.

17. The compound according to claim 14 or a pharmaceutically acceptable salt thereof wherein $R^3$ is selected from the group consisting of methyl, ethyl, propyl, isopropyl, butyl, $CH_2OH$, $CH_2CH_2OH$, $CH_2CN$, $CH_2CF_3$, $CH_2CH_2F$, $CH_2CH_2CF_3$, $CH_2CHF_2$, and $CH(CH_2OH)CH_3$.

18. The compound according to claim 14 or a pharmaceutically acceptable salt thereof wherein $R^1$ is optionally substituted $C_{1-6}$alkyl selected from the group consisting of $CH_3$, $CH_2OH$, $CH_2CH_2OH$, $CH_2CN$, $CH_2CF_3$, $CH_2CH_2F$, $CH_2CH_2CF_3$, $CH(CH_2OH)CH_3$, $R^2$ and $R^3$ are methyl, and $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $CF_2CF_3$, cyclobutyl, cyclopropyl said groups optionally substituted with 1 to 3 groups of $C_{1-6}$alkyl or halo.

19. The compound according to claim 1 wherein $R^3$ and $R^{3a}$ combine with the carbon atom to which they are attached to form a $C_{3-6}$cycloalkyl, or $C_{4-10}$ heterocycloalkyl, said alkyl, cycloalkyl, and heterocycloalkyl optionally substituted with 1 to 3 groups of $R^a$.

20. A compound which is selected from the group consisting of:
(R)-5-Methyl-3-(1-(4-(trifluoromethyl)phenyl)ethyl)-1H-pyrazolo[4,3-d]pyrimidin-7(6H)-one,
(S)-5-Methyl-3-(1-(4-(trifluoromethyl)phenyl)ethyl)-1H-pyrazolo[4,3-d]pyrimidin-7(6H)-one,
(R)-1-(2-Hydroxyethyl)-5-methyl-3-(1-(4-(trifluoromethyl)phenyl)ethyl)-1H-pyrazolo[4,3-d]pyrimidin-7(6H)-one,
(S)-1-(2-Hydroxyethyl)-5-methyl-3-(1-(4-(trifluoromethyl)phenyl)ethyl)-1H-pyrazolo[4,3-d]pyrimidin-7(6H)-one,
(R)-3-(1-(4-(tert-Butyl)phenyl)ethyl)-1-(2-hydroxyethyl)-5-methyl-1,6-dihydro-7H-pyrazolo[4,3-d]pyrimidin-7-one,
(S)-3-(1-(4-(tert-Butyl)phenyl)ethyl)-1-(2-hydroxyethyl)-5-methyl-1,6-dihydro-7H-pyrazolo[4,3-d]pyrimidin-7-one, (R)-3-(1-(3-Fluoro-4-(trifluoromethyl)phenyl)ethyl)-1-(2-hydroxyethyl)-5-methyl-1,6-dihydro-7H-pyrazolo[4,3-d]pyrimidin-7-one,
(S)-3-(1-(3-Fluoro-4-(trifluoromethyl)phenyl)ethyl)-1-(2-hydroxyethyl)-5-methyl-1,6-dihydro-7H-pyrazolo[4,3-d]pyrimidin-7-one,
(R)-3-(1-(2-Fluoro-3-(trifluoromethyl)phenyl)ethyl)-1-(2-hydroxyethyl)-5-methyl-1,6-dihydro-7H-pyrazolo[4,3-d]pyrimidin-7-one,
(S)-3-(1-(2-Fluoro-3-(trifluoromethyl)phenyl)ethyl)-1-(2-hydroxyethyl)-5-methyl-1,6-dihydro-7H-pyrazolo[4,3-d]pyrimidin-7-one,
(R)-5-Methyl-1-(2,2,2-trifluoroethyl)-3-(1-(4-(trifluoromethyl)phenyl)ethyl)-1H-pyrazolo[4,3-d]pyrimidin-7(6H)-one,
(S)-5-Methyl-1-(2,2,2-trifluoroethyl)-3-(1-(4-(trifluoromethyl)phenyl)ethyl)-1H-pyrazolo[4,3-d]pyrimidin-7(6H)-one
(R)-1-(2-Fluoroethyl)-5-methyl-3-(1-(4-(trifluoromethyl)phenyl)ethyl)-1H-pyrazolo[4,3-d]pyrimidin-7(6H)-one,
(S)-1-(2-Fluoroethyl)-5-methyl-3-(1-(4-(trifluoromethyl)phenyl)ethyl)-1H-pyrazolo[4,3-d]pyrimidin-7(6H)-one
(R)-3-(1-(4-(tert-Butyl)phenyl)ethyl)-1-(2-fluoroethyl)-5-methyl-1,6-dihydro-7H-pyrazolo[4,3-d]pyrimidin-7-one,
(S)-3-(1-(4-(tert-Butyl)phenyl)ethyl)-1-(2-fluoroethyl)-5-methyl-1,6-dihydro-7H-pyrazolo[4,3-d]pyrimidin-7-one,
(R)-3-(1-(3-Fluoro-4-(trifluoromethyl)phenyl)ethyl)-1-(2-fluoroethyl)-5-methyl-1,6-dihydro-7H-pyrazolo[4,3-d]pyrimidin-7-one,
(S)-3-(1-(3-Fluoro-4-(trifluoromethyl)phenyl)ethyl)-1-(2-fluoroethyl)-5-methyl-1,6-dihydro-7H-pyrazolo[4,3-d]pyrimidin-7-one,
(R)-5-Methyl-3-(1-(4-(trifluoromethyl)phenyl)ethyl)-1-(3,3,3-trifluoropropyl)-1H-pyrazolo[4,3-d]pyrimidin-7(6H)-one,
(S)-5-Methyl-3-(1-(4-(trifluoromethyl)phenyl)ethyl)-1-(3,3,3-trifluoropropyl)-1H-pyrazolo[4,3-d]pyrimidin-7(6H)-one
1-((R)-1-Hydroxypropan-2-yl)-5-methyl-3-((S)-1-(4-(trifluoromethyl)phenyl)ethyl)-1,6-dihydro-7H-pyrazolo[4,3-d]pyrimidin-7-one,
1-((S)-1-Hydroxypropan-2-yl)-5-methyl-3-((R)-1-(4-(trifluoromethyl)phenyl)ethyl)-1,6-dihydro-7H-pyrazolo[4,3-d]pyrimidin-7-one,
1,5-Dimethyl-3-(1-(4-(trifluoromethyl)phenyl)ethyl)-1,6-dihydro-7H-pyrazolo[4,3-d]pyrimidin-7-one,
(R)-2,5-Dimethyl-7-(1-(4-(trifluoromethyl)phenyl)ethyl)imidazo[5,1-f][1,2,4]triazin-4(3H)-one,
(S)-2,5-Dimethyl-7-(1-(4-(trifluoromethyl)phenyl)ethyl)imidazo[5,1-f][1,2,4]triazin-4(3H)-one
(R)-5-(Hydroxymethyl)-2-methyl-7-(1-(4-(trifluoromethyl)phenyl)ethyl)imidazo[5,1-f][1,2,4]triazin-4(3H)-one,
(S)-5-(Hydroxymethyl)-2-methyl-7-(1-(4-(trifluoromethyl)phenyl)ethyl)imidazo[5,1-f][1,2,4]triazin-4(3H)-one
(R)-7-(1-(2-fluoro-4-(trifluoromethyl)phenyl)ethyl)-5-(hydroxymethyl)-2-methylimidazo[5,1-f][1,2,4]triazin-4(3H)-one,
(S)-7-(1-(2-fluoro-4-(trifluoromethyl)phenyl)ethyl)-5-(hydroxymethyl)-2-methylimidazo[5,1-f][1,2,4]triazin-4(3H)-one,
(R)-5-(hydroxymethyl)-2-methyl-7-(1-(4-(trifluoromethoxy)phenyl)ethyl)imidazo[5,1-f][1,2,4]triazin-4(3H)-one,
(S)-5-(hydroxymethyl)-2-methyl-7-(1-(4-(trifluoromethoxy)phenyl)ethyl)imidazo[5,1-f][1,2,4]triazin-4(3H)-one,
(R)-7-(1-(3-fluoro-4-(trifluoromethyl)phenyl)ethyl)-5-(hydroxymethyl)-2-methylimidazo[5,1-f][1,2,4]triazin-4(3H)-one,
(S)-7-(1-(3-fluoro-4-(trifluoromethyl)phenyl)ethyl)-5-(hydroxymethyl)-2-methylimidazo[5,1-f][1,2,4]triazin-4(3H)-one,
(R)-5-(hydroxymethyl)-2-methyl-7-(1-(4-(1-methylcyclopropyl)phenyl)ethyl)imidazo[5,1-f][1,2,4]triazin-4(3H)-one,
(S)-5-(hydroxymethyl)-2-methyl-7-(1-(4-(1-methylcyclopropyl)phenyl)ethyl)imidazo[5,1-f][1,2,4]triazin-4(3H)-one,
2-(2-Methyl-4-oxo-7-(1-(4-(trifluoromethyl)phenyl)ethyl)-3,4-dihydroimidazo[5,1-f][1,2,4]triazin-5-yl)acetonitrile,
(R)-5-(2-hydroxyethyl)-2-methyl-7-(1-(4-(trifluoromethyl)phenyl)ethyl)imidazo[5,1-f][1,2,4]triazin-4(3H)-one,
(5)-5-(2-hydroxyethyl)-2-methyl-7-(1-(4-(trifluoromethyl)phenyl)ethyl)imidazo[5,1-f][1,2,4]triazin-4(3H)-one
or a pharmaceutically acceptable salt thereof.

21. A pharmaceutical composition which comprises a pharmaceutically acceptable carrier and a compound of claim 1 or a pharmaceutically acceptable salt thereof.

22. A method of treating a disorder selected from psychotic disorders, delusional disorders and drug induced psychosis; anxiety disorders, movement disorders, mood disorders, Alzheimer's disease, schizophrenia, migraines, Parkinson's disease, Parkinson's disease dementia (PDD), Huntingtons's disease, and neurodegenerative disorders comprising administering a compound of claim 1 or a pharmaceutically acceptable salt thereof.

* * * * *